US011229433B2

(12) United States Patent
Schings et al.

(10) Patent No.: US 11,229,433 B2
(45) Date of Patent: Jan. 25, 2022

(54) LINEAR SURGICAL STAPLER

(71) Applicant: Ethicon LLC, Guaynabo, PR (US)

(72) Inventors: Brian D. Schings, Cincinnati, OH (US); William J. White, West Chester, OH (US); Jason D. Jones, Cincinnati, OH (US); Carol J. Wynn, Kings Mills, OH (US); Anil K. Nalagatla, Mason, OH (US); Andrew C. Deck, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 127 days.

(21) Appl. No.: 16/537,005

(22) Filed: Aug. 9, 2019

(65) Prior Publication Data

US 2021/0038223 A1 Feb. 11, 2021

(51) Int. Cl.
*A61B 17/072* (2006.01)

(52) U.S. Cl.
CPC ........... *A61B 17/07207* (2013.01); *A61B 2017/07257* (2013.01); *A61B 2017/07271* (2013.01)

(58) Field of Classification Search
CPC .......... A61B 17/07207; A61B 17/0644; A61B 17/0684; A61B 17/115; A61B 17/105; A61B 17/068; A61B 2017/07257; A61B 2017/07271; A61B 2017/07285; A61B 2017/07242; A61B 2017/07278; A61B 2017/07228; A61B 2090/034; A61B 2090/0814

(Continued)

(56) References Cited

U.S. PATENT DOCUMENTS 5,415,334 A  5/1995 Williamson et al.
8,485,412 B2 * 7/2013 Shelton, IV ......... A61B 17/105
                                                 227/176.1

(Continued)

FOREIGN PATENT DOCUMENTS

EP  2 586 379 A1  5/2013
EP  2 932 914 A1  10/2015

(Continued)

OTHER PUBLICATIONS

European Search Report, Partial, and Provisional Written Opinion dated Dec. 16, 2020 for Application No. EP 20190310.1, 18 pgs.

(Continued)

*Primary Examiner* — Stephen F. Gerrity
*Assistant Examiner* — Linda J Hodge
(74) *Attorney, Agent, or Firm* — Frost Brown Todd LLC

(57) ABSTRACT

A staple cartridge configured for use with a surgical stapler includes a cartridge body, a deck defined configured to compress tissue against an anvil of the surgical stapler, and a plurality of staple openings formed in the deck. A plurality of staples is disposed within the staple openings, with each staple having a pair of legs. A plurality of staple drivers is also disposed within the staple openings, with the staple drivers being actuatable to drive the staples through tissue and against the anvil to form the legs. Each of the staple drivers includes a driver body, a first pocket disposed on a first lateral side of the driver body, and a second pocket disposed on a second lateral side of the driver body. The first and second pockets are configured to receive the legs of the respective staple when the legs are formed against the anvil.

20 Claims, 35 Drawing Sheets

(58) Field of Classification Search
USPC .......................................... 227/175.1–182.1
See application file for complete search history.

(56) References Cited

U.S. PATENT DOCUMENTS

| | | | |
|---|---|---|---|
| 9,572,574 B2 | 2/2017 | Shelton, IV et al. | |
| 10,631,866 B2 | 4/2020 | Laurent et al. | |
| 2012/0080498 A1* | 4/2012 | Shelton, IV | A61B 17/105 227/178.1 |
| 2013/0240595 A1* | 9/2013 | Penna | A61B 17/07207 227/175.1 |
| 2015/0173755 A1* | 6/2015 | Baxter, III | A61B 17/07207 227/180.1 |
| 2015/0297235 A1* | 10/2015 | Harris | G06F 11/1425 227/176.1 |
| 2019/0239882 A1 | 8/2019 | McLain et al. | |
| 2019/0239883 A1 | 8/2019 | Baxter, III et al. | |
| 2019/0239884 A1 | 8/2019 | Baxter, III et al. | |
| 2019/0239885 A1 | 8/2019 | Stokes et al. | |
| 2019/0239886 A1 | 8/2019 | Jones et al. | |
| 2020/0046350 A1 | 2/2020 | Deck et al. | |
| 2020/0046351 A1 | 2/2020 | Jones et al. | |
| 2020/0046353 A1 | 2/2020 | Deck et al. | |
| 2020/0113561 A1 | 4/2020 | Schings et al. | |
| 2020/0113562 A1 | 4/2020 | Schings et al. | |

FOREIGN PATENT DOCUMENTS

| | | |
|---|---|---|
| EP | 3 061 408 A1 | 8/2016 |
| EP | 3 123 951 A1 | 2/2017 |

OTHER PUBLICATIONS

European Search Report, Extended, and Written Opinion dated Mar. 22, 2021 for Application No. EP 20190310.1, 17 pgs.
International Search Report and Written Opinion dated Dec. 17, 2020 for Application No. PCT/IB2020/057330, 21 pgs.

* cited by examiner

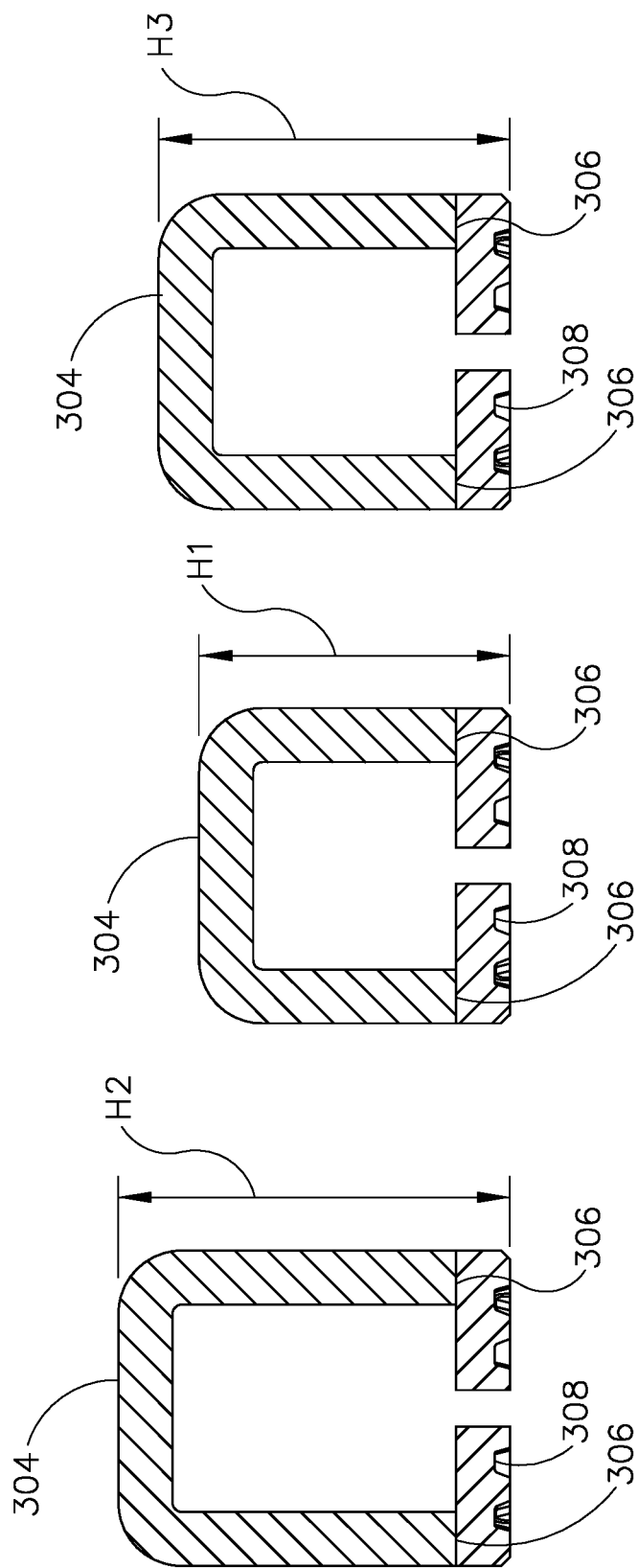

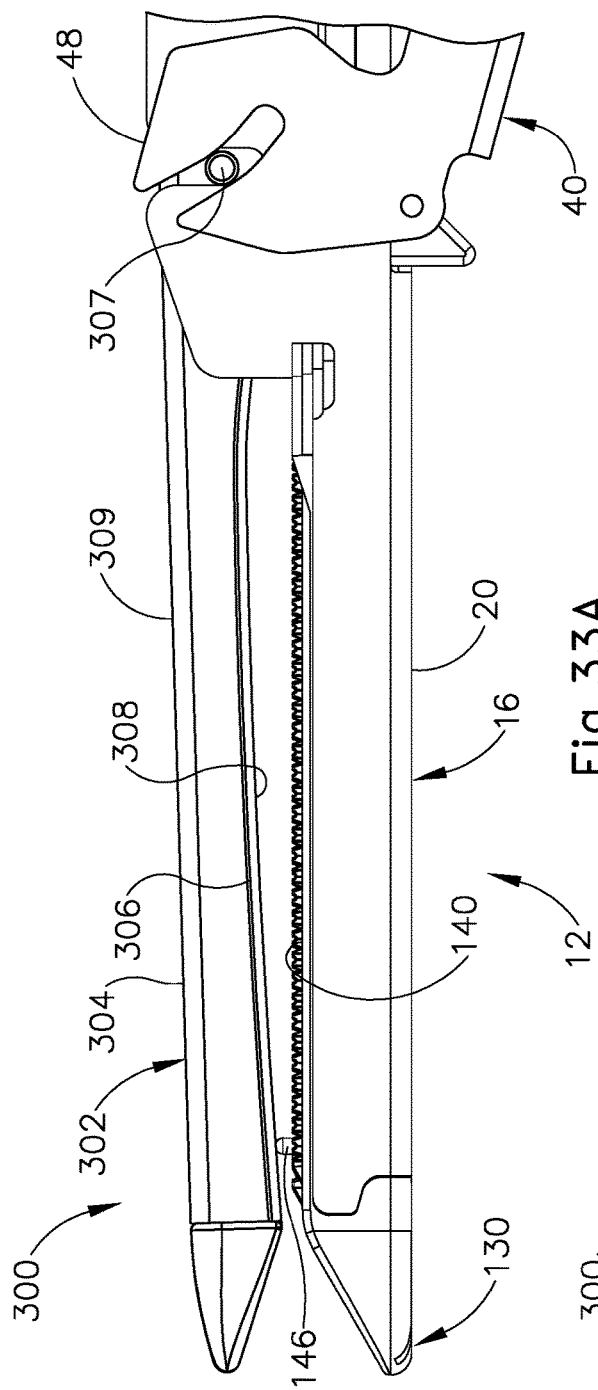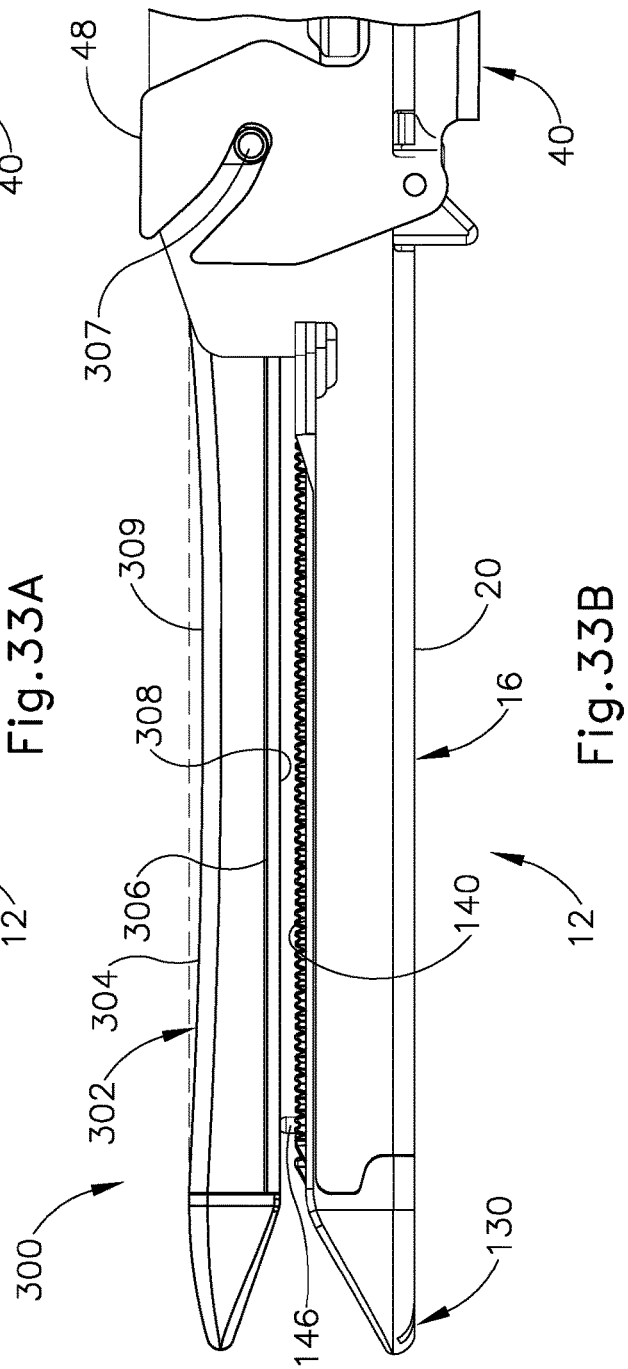

LINEAR SURGICAL STAPLER

BACKGROUND

In some surgical operations, such as a gastrointestinal anastomosis, it may be desirable to clamp down on one or more layers of tissue, cut through the clamped layers, and simultaneously drive staples through the layers to substantially seal the severed layers of tissue together near their severed ends. One such instrument that may be used in such operations is a linear surgical stapler, also referred to as a "linear cutter." A linear surgical stapler generally includes a first half (referred to as a "cartridge half" or "reload half") having a distal jaw configured to support a staple cartridge (or "reload"), and a second half (referred to as an "anvil half") having a distal jaw that supports an anvil surface having staple forming features. The stapler further includes a moveable clamp lever configured to releasably clamp the stapler halves together. The stapler halves are configured to pivot relative to one another to receive and clamp tissue between the two distal jaws when the clamp lever is closed. A firing assembly of the stapler is configured to be actuated to cut the clamped layers and simultaneously drive staples through the tissue on either side of the cut line. After firing the stapler, the clamp lever may be opened, and the stapler halves separated to release the severed and stapled tissue.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 32A depicts a cross-sectional end view of the distal jaw portion of the anvil half of FIG. 31, taken along section line 32A-32A in FIG. 31, with a distal tip structure being omitted;

FIG. 32B depicts a cross-sectional end view of the distal jaw portion of the anvil half of FIG. 31, taken along section line 32B-32B in FIG. 31;

FIG. 32C depicts a cross-sectional end view of the distal jaw portion of the anvil half of FIG. 31, taken along section line 32C-32C in FIG. 31;

FIG. 33A depicts a side elevational view of a distal portion of a linear surgical stapler having the anvil half of FIG. 31 and the cartridge half of FIG. 1, with shrouds of the stapler halves being omitted, showing the stapler halves in a partially clamped state in which the anvil plate exhibits a concavely curved configuration;

FIG. 33B depicts a side elevational view of the distal portion of the linear surgical stapler of FIG. 33A, showing the stapler halves in a fully clamped state in which the anvil plate assumes a straight configuration.

Figure 1:
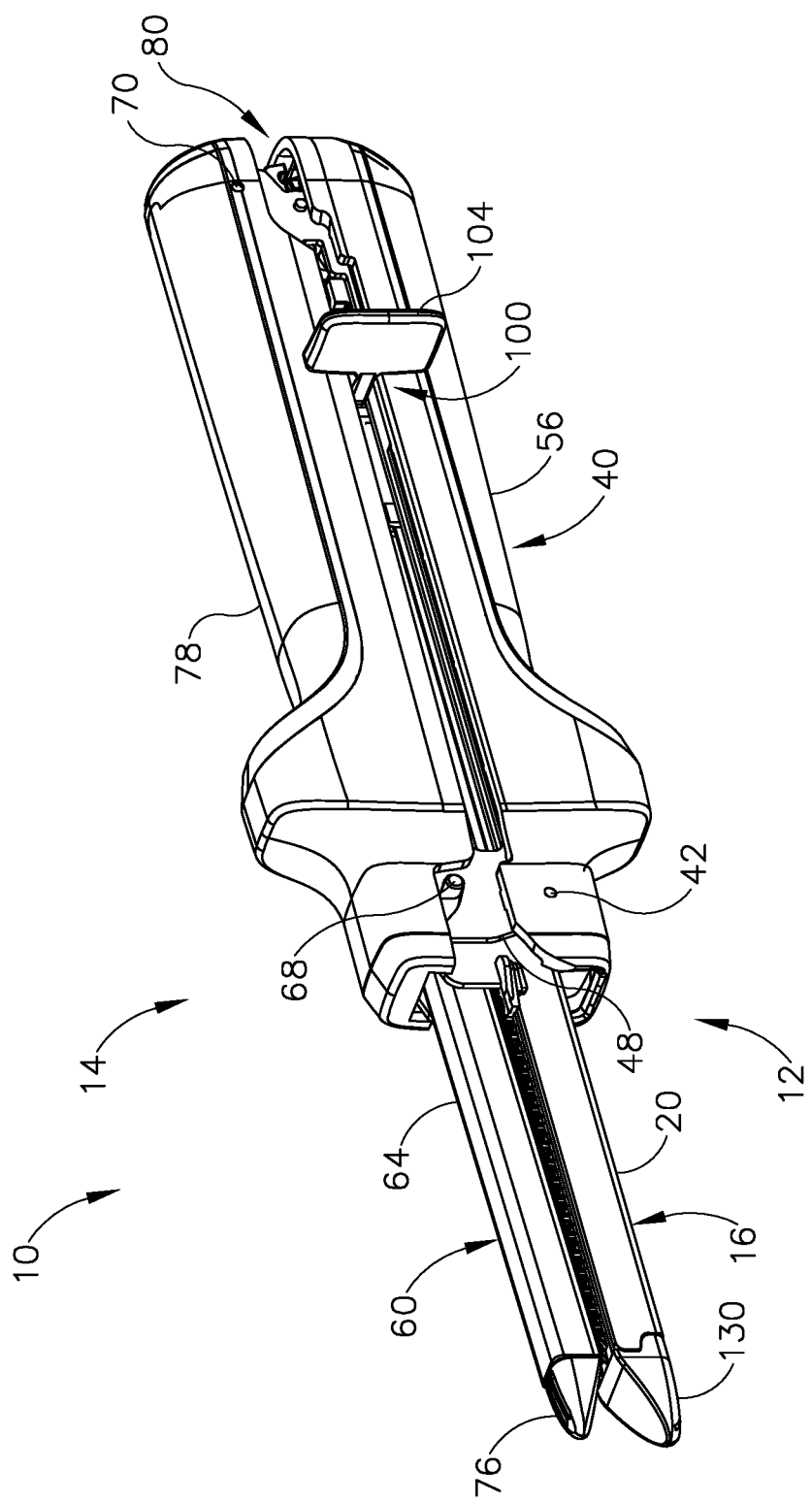
FIG. 1 depicts a perspective view of an exemplary linear surgical stapler, showing a cartridge half and an anvil half of the stapler coupled together with a clamp lever of the cartridge half in a fully closed position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Linear Surgical Stapler

A. Overview of Linear Surgical Stapler

Figure 2:
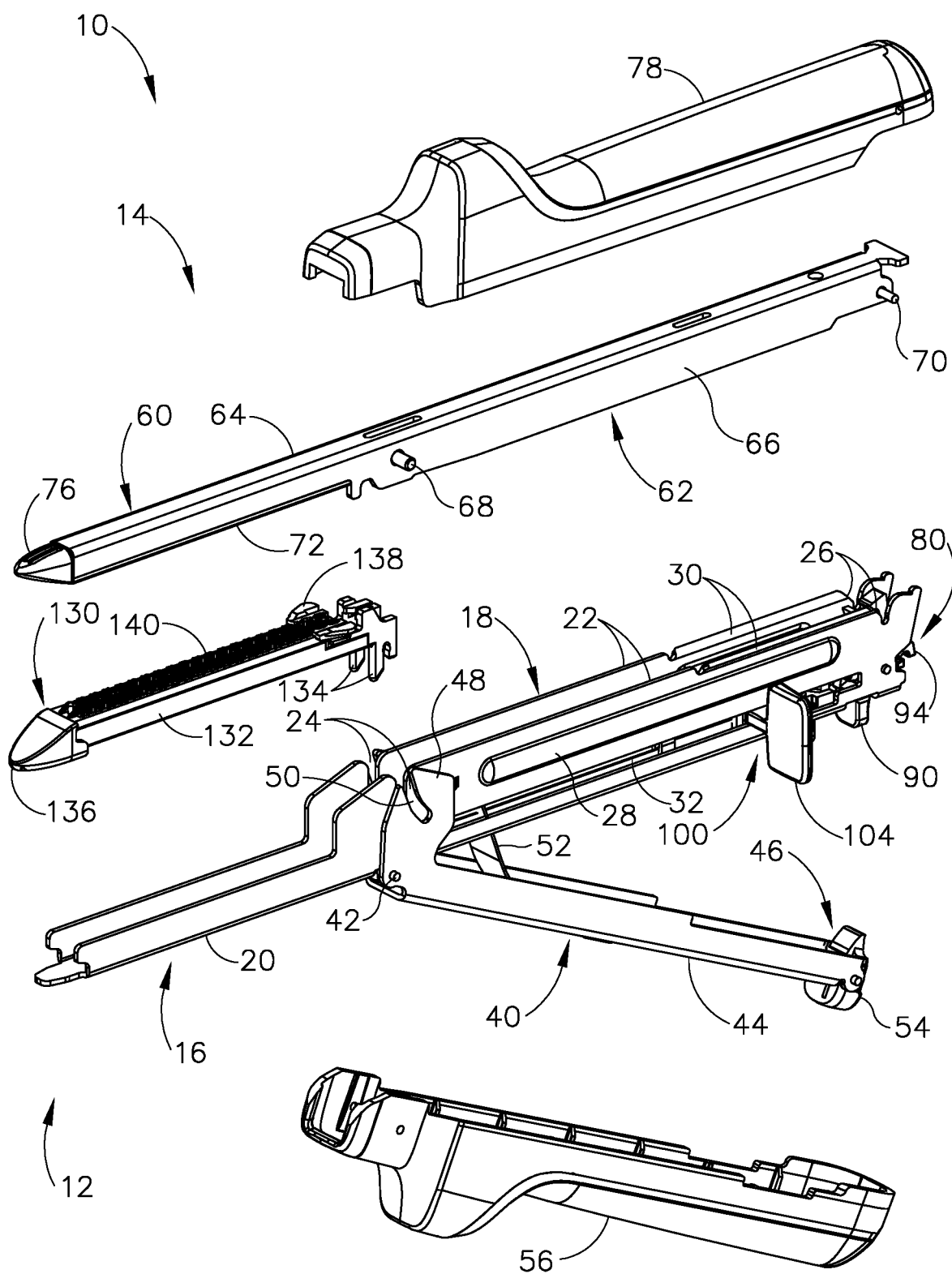
FIG. 2 depicts an exploded perspective view of the linear surgical stapler of FIG. 1.

FIGS. 1-2 show an exemplary linear surgical stapler (10) (also referred to as a "linear cutter") suitable for use in a variety of cutting and stapling procedures, such as a gastrointestinal anastomosis procedure. Linear surgical stapler (10) includes a cartridge half (12) (also referred to as a "reload half") and an anvil half (14) configured to releasably couple together to clamp tissue therebetween for simultaneous cutting and stapling of the clamped tissue.

Cartridge half (12) includes an elongate cartridge channel (16) having a proximal frame portion (18) and a distal jaw portion (20). Proximal frame portion (18) slidably retains a firing assembly (100) and includes a laterally opposed pair of upright side flanges (22). Each side flange (22) includes a vertical slot (24) arranged at a distal end thereof, and a tapered notch (26) arranged at a proximal end thereof. An outwardly projecting stiffening rib (28) extends longitudinally between the distal slot (24) and proximal notch (26) of each side flange (22) and is configured to provide the side flange (22) with enhanced stiffness. An outwardly flared upper segment (30) defines an upper edge of a proximal portion of each side flange (22) and is configured to facilitate receipt of anvil half (14) by cartridge half (12). Each side flange (22) further includes an elongate firing slot (32) extending longitudinally between proximal notch (26) and distal slot (24) along a lower side of side flange (22).

Elongate firing slots (32) are configured to guide firing assembly (100) between proximal and distal positions. Firing assembly (100) is described in greater detail below in connection with FIG. 4. Distal jaw portion (20) of cartridge channel (16) is configured to receive a staple cartridge (130) (or "reload"), which is described in great detail below in connection with FIGS. 6-20.

Cartridge half (12) further includes a clamp lever (40) (also referred to as a "latch lever") pivotably coupled to cartridge channel (16) with a clamp lever pivot pin (42), which is arranged in approximate alignment with distal slots (24) of cartridge channel side flanges (22). Clamp lever (40) includes an elongate lever arm (44) having a free proximal end (46) and a distal end that is pivotably coupled to a lower portion of cartridge channel (16) with pivot pin (42). A pair of opposed jaws (48) extend distally from the distal end of lever arm (44) alongside cartridge channel side flanges (22). Each jaw (48) includes a curved slot (50) having a closed proximal end and an open distal end configured to receive a latch pin (68) of anvil half (14), as described below.

Figure 3:
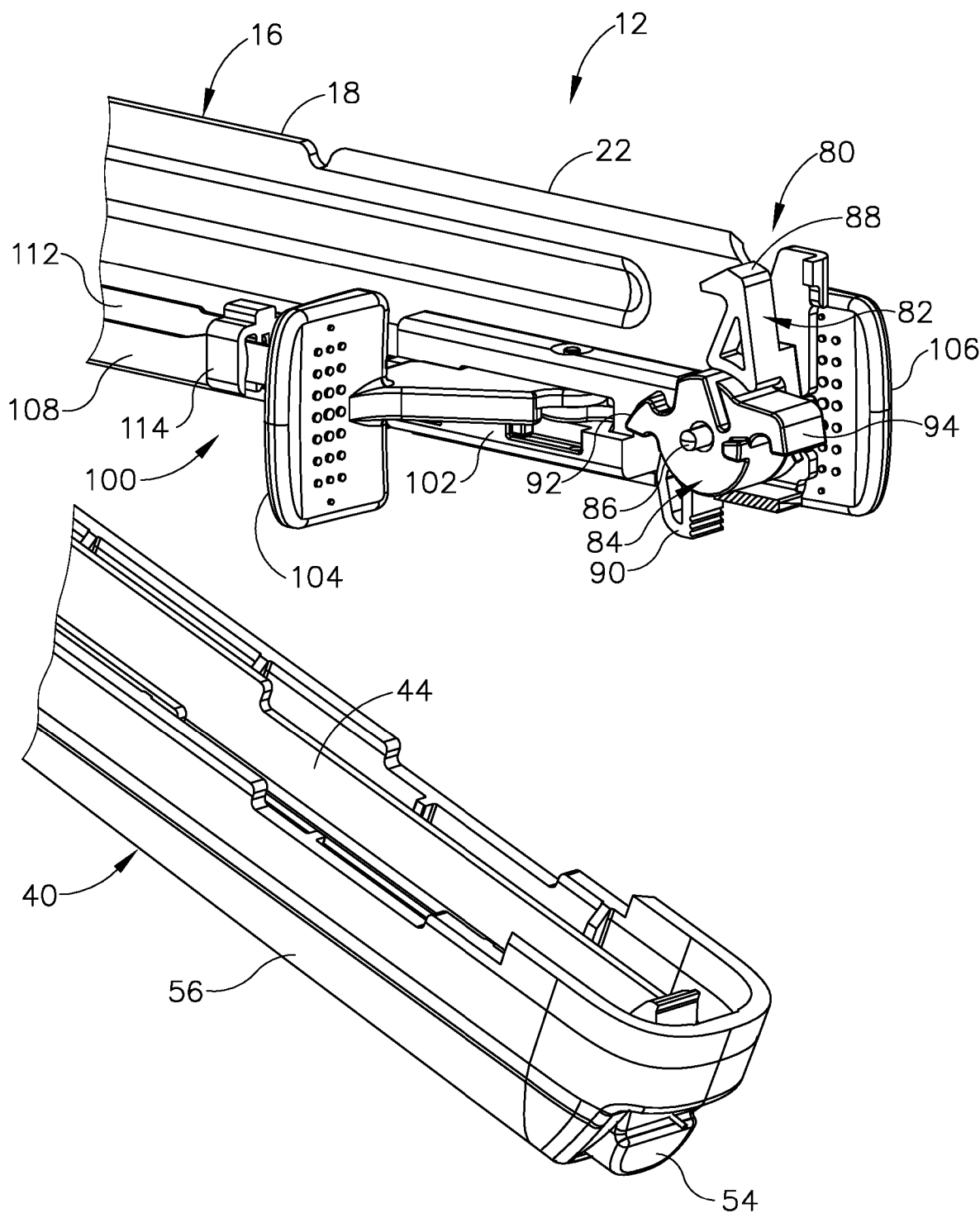
FIG. 3 depicts a perspective view of a proximal portion of the cartridge half of the linear surgical stapler of FIG. 1, showing a cartridge channel in cross-section and the clamp lever in an open position to reveal internal features of the cartridge half.

Clamp lever (40) is operable to pivot relative to cartridge channel (16) between an open position in which proximal end (46) of lever arm (44) is spaced from cartridge channel frame portion (18), and a closed position in which proximal end (46) confronts cartridge channel frame portion (18). Actuation of clamp lever (40) from the open position to the closed position operates to capture the opposed lateral ends of latch pin (68) within clamp lever jaw slots (50), and thereby clamp anvil half (14) against cartridge half (12), as shown and described below in connection with FIGS. 5C-5D. In that regard, the curvature of each jaw slot (50) defines respective upper and lower camming surfaces configured to engage and draw the respective lateral end of latch pin (68) toward cartridge channel (16) as clamp lever (40) is pivotably closed. A resilient member shown in the form of a flat spring (52) biases lever arm (44) toward the open position. Accordingly, flat spring (52) promotes disengagement of clamp lever jaws (48) from anvil half latch pin (68) upon initial advancement of clamp lever (40) from the closed position toward the open position. As best shown in FIGS. 2 and 3, clamp lever (40) further includes a latch member (54) arranged at proximal end (46) of lever arm (44). Clamp lever latch member (54) is configured to resiliently and releasably engage a proximal end of cartridge channel frame portion (18) and thereby releasably retain clamp lever (40) in the closed position, for instance while stapler (10) is being fired.

Anvil half (14) of linear surgical stapler (10) includes an elongate anvil channel (60) having a proximal frame portion (62) and a distal jaw portion (64). Proximal frame portion (62) includes a laterally opposed pair of upright side flanges (66) that are configured to be received between cartridge channel side flanges (22) when anvil half (14) is coupled with cartridge half (12). A distal latch projection in the form of latch pin (68) extends laterally through the distal ends of anvil channel side flanges (66), and a proximal pivot projection in the form of a proximal pin (70) extends laterally through the proximal ends of anvil channel side flanges (66). Anvil pins (68, 70) are configured to facilitate coupling of anvil half (14) with cartridge half (12), as described below.

Distal jaw portion (64) of anvil half (14) supports an anvil plate (72) that defines an anvil surface having a plurality of staple forming pockets (74) (see FIG. 15) configured to deform legs (174) of staples (170) ejected by staple cartridge (130) when stapler (10) is fired, for example as described in greater detail below. In some versions, the anvil surface may be formed integrally with distal jaw portion (64). Distal jaw portion (64) of anvil half (14) additionally supports a tapered distal tip member (76). In some versions, distal tip member (76) may be selectively extendable relative to distal jaw portion (64) in accordance with the teachings of U.S. patent application Ser. No. 16/165,587, entitled "Decoupling Mechanism for Linear Surgical Stapler," filed on Oct. 19, 2018, issued as U.S. Pat. No. 11,033,266 on Jun. 15, 2021, the disclosure of which is incorporated by reference herein.

As shown in FIG. 2, linear surgical stapler (10) further includes a plurality of shrouds (56, 78) that cover select portions of stapler (10) and promote effective grip and manipulation of stapler (10) by an operator during use. In the present example, a clamp lever shroud (56) is affixed to and covers an outwardly facing side of clamp lever (40) such that clamp lever shroud (56) is configured to pivot with clamp lever (40) relative to cartridge channel (16). Additionally, an anvil shroud (78) is affixed to and covers an outwardly facing side of anvil channel (60). In some versions, anvil shroud (78) may be coupled with anvil channel (60) in accordance with the teachings of U.S. patent application Ser. No. 16/102,170, entitled "Clamping Assembly for Linear Surgical Stapler," filed on Aug. 13, 2018, published as U.S. Pub. No. 2020/0046353 on Feb. 13, 2020, the disclosure of which is incorporated by reference herein. It will be appreciated that in other versions, shrouds (56, 78) may be coupled with clamp lever (40) and anvil channel (60) in a variety of other suitable manners readily apparent to those of ordinary skill in the art.

As shown best in FIG. 3, a proximal end of cartridge half (12) includes a retaining assembly (80) configured to releasably retain portions of anvil half (14) and firing assembly (100). Retaining assembly (80) of the present example includes an anvil latch member (82) and a detent member (84), both of which are rotatably coupled with a proximal end of cartridge channel (16) via a laterally extending pin (86) arranged proximally of firing slots (32). A torsion spring (not shown) is configured to resiliently bias anvil latch member (82) and detent member in opposite rotational directions about the lateral axis defined by pin (86).

Anvil latch member (82) includes an upper finger (88) configured to releasably capture proximal anvil pin (70) when pin (70) is directed into proximal tapered notches (26) of cartridge channel (16), thereby coupling the proximal ends of stapler halves (12, 14). A lower end of anvil latch member (82) defines a release button (90) configured to be depressed by the operator when clamp lever (40) is in the open position to release proximal pin (70) from latch finger (88) and thereby permit separation of the proximal ends of stapler halves (12, 14). Detent member (84) includes a distal finger (88) configured to releasably capture the proximal end of a slide block (102) of firing assembly (100) when firing assembly (100) us in a proximal home position, shown in FIG. 3. Detent member (84) further includes a proximal hook (94) configured to releasably capture an upper tip of clamp lever latch member (54) while slide block (102) is positioned distally of its proximal home position, thereby preventing actuation of clamp lever latch member (54) and opening of clamp lever (40) during firing of stapler (10). When firing assembly (100) is in its proximal home position (i.e., before or after firing of stapler (10)), proximal hook (94) of detent member (84) permits clamp lever latch member (54) to rotatably disengage proximal frame portion (18) of cartridge channel (16) in response to actuation by the operator. As a result, clamp lever (40) may then be opened. Retaining assembly (80) and related components of cartridge half (12) may be further configured and operable in accordance with at least some of the teachings of U.S. patent application Ser. No. 16/102,164, entitled "Firing System for Linear Surgical Stapler," filed on Aug. 13, 2018, issued as U.S. Pub. No. 10,898,187 on Jan. 26, 2021, the disclosure of which is incorporated by reference herein.

Figure 4:
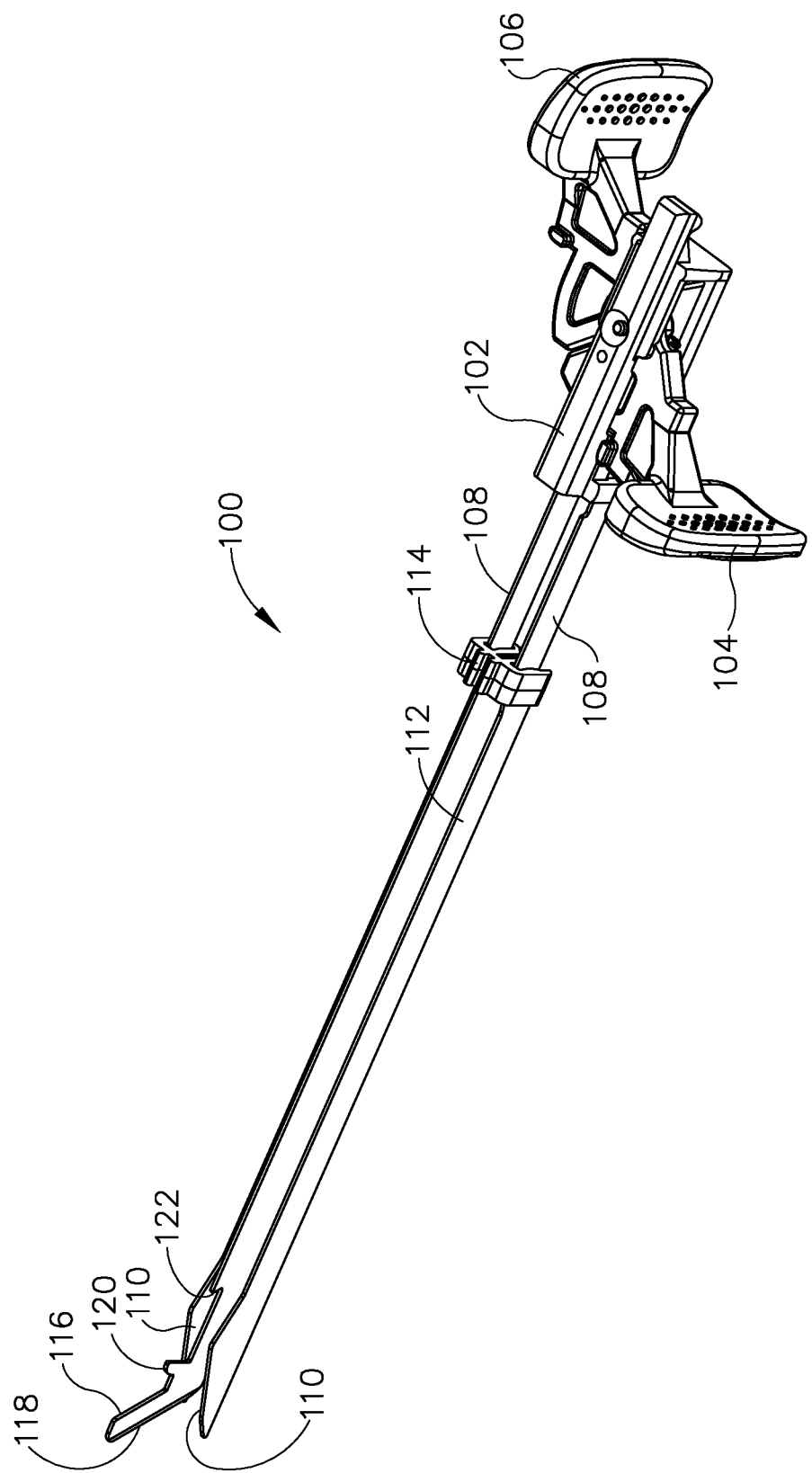
FIG. 4 depicts a top perspective view of a firing assembly of the linear surgical stapler of FIG. 1.

As shown best in FIG. 4, firing assembly (100) of cartridge half (12) includes slide block (102), a pair of actuators (104, 106) (or "firing knobs") pivotably coupled to slide block (102), and a plurality of elongate beams (108, 112) extending distally from slide block (102). A pair of side beams (108) are coupled at their proximal ends to a distal end of slide block (102) and terminate distally in a pair of cam ramps (110). Cam ramps (110) are configured to engage the undersides of staple drivers (180) housed within staple cartridge (130) (see FIG. 7) and actuate staple drivers (180) upwardly to thereby drive (or "fire") staples (170) from cartridge (130) into tissue clamped between staple cartridge (130) and anvil plate (72). A center beam (112) is coupled with side beams (108) via a bridge member (114) (or "knife block") spaced distally from slide block (102). Center beam (112) terminates distally in a distally angled knife member (116) having a distal cutting edge (118) configured to cut tissue clamped between the distal portions of stapler halves (12, 14). A distal portion of center beam (112) additionally includes an upwardly projecting stop element (120) proximal to knife member (116), and a distally facing lockout projection (122) proximal to stop element (120).

Each actuator (104, 106) of firing assembly (100) is configured and rotatable relative to slide block (102) between a deployed position and a retracted position such that only one actuator (104, 106) may be deployed at a time, for example as described in greater detail in U.S. patent application Ser. No. 16/102,164, issued as U.S. Pat. No. 10,898,187 on Jan. 26, 2021, incorporated by reference above. In the deployed position, an actuator (104, 106) may be driven distally by an operator to actuate firing assembly (100) distally through stapler (10) and thereby simultaneously cut and staple tissue clamped between stapler halves (12, 14).

B. Exemplary Use of Linear Surgical Stapler

Figure 5A:
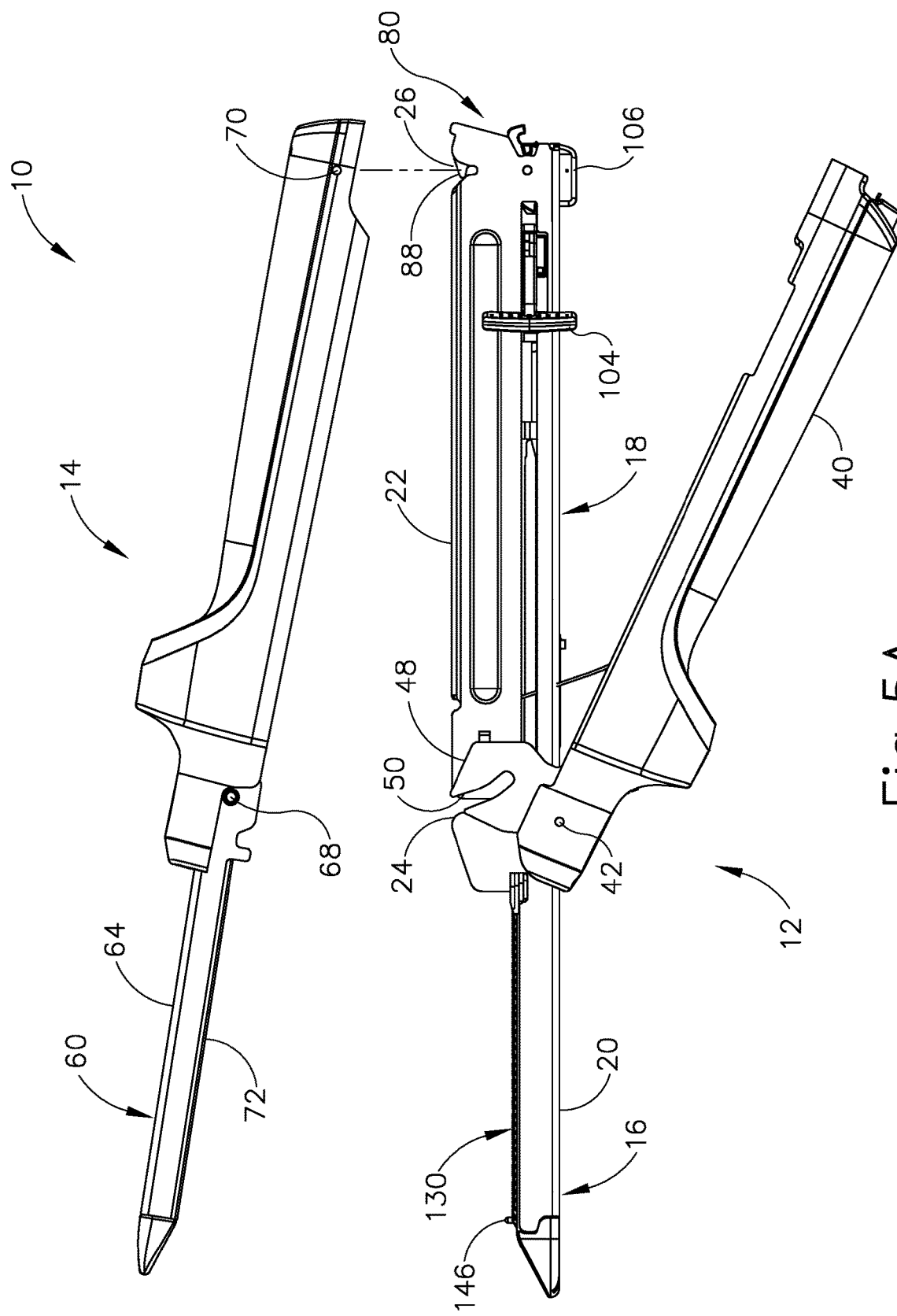
FIG. 5A depicts a side elevational view of the linear surgical stapler of FIG. 1, showing the stapler halves separated from one another.

FIGS. 5A-5E show exemplary coupling of stapler halves (12, 14) and subsequent firing of assembled stapler (10) during a surgical procedure. As shown in FIG. 5A, clamp lever (40) of cartridge half (12) is provided in the open position so that jaw slots (50) align with vertical slots (24) of cartridge channel side flanges (22). Additionally, firing assembly (100) is maintained in its proximal home position by detent member (84) of retaining assembly (80), as shown in FIG. 3 described above. At this stage, a section of tissue (not shown) to be stapled and cut may be positioned over the top of staple cartridge (130) disposed in distal jaw portion (20) of cartridge half (12). Alternatively, the tissue may be positioned over staple cartridge (130) following coupling of the proximal ends of stapler halves (12, 14), described below.

Figure 5B:
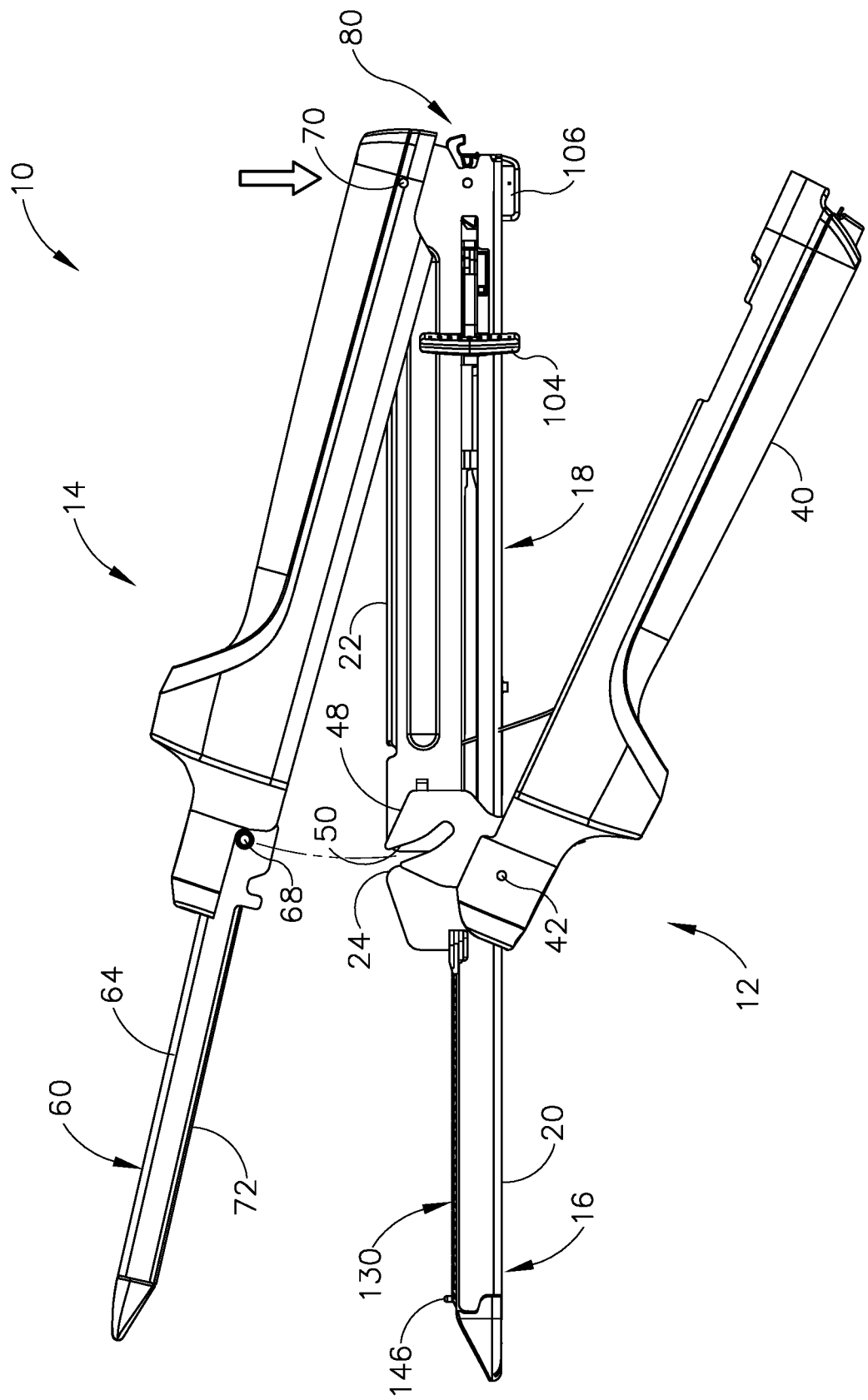
FIG. 5B depicts a side elevational view of the linear surgical stapler of FIG. 1, showing proximal ends of the stapler halves coupled together.
Figure 5C:
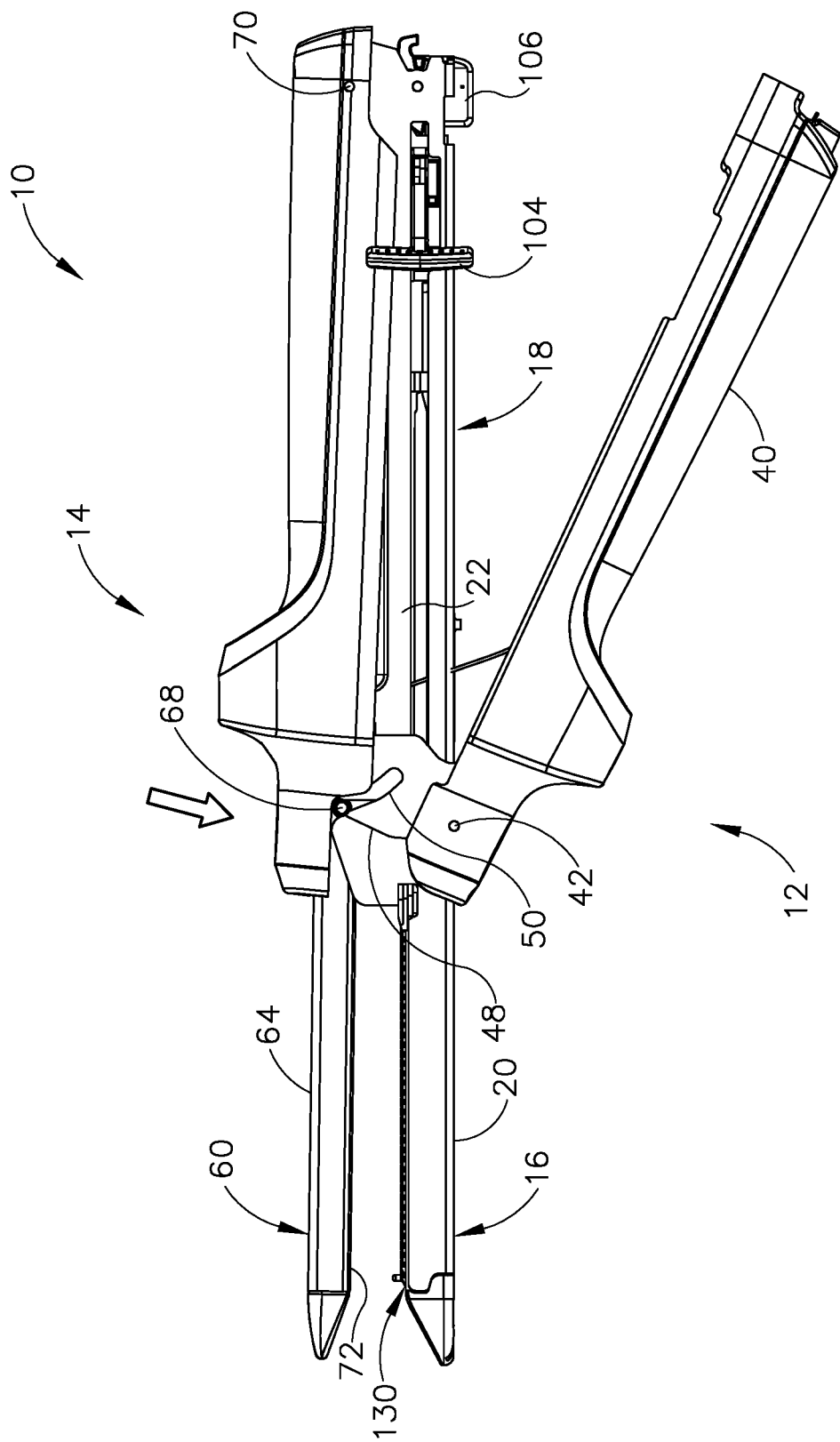
FIG. 5C depicts a side elevational view of the linear surgical stapler of FIG. 1, showing a distal pin of the anvil half being received by clamp lever jaws of the cartridge half.

As shown in FIG. 5A-5B, the proximal ends of stapler halves (12, 14) are aligned with one another and proximal anvil pin (70) is directed downwardly into proximal tapered notches (26) of cartridge channel (16) to engage upper finger (88) of anvil latch member (82). This engagement forces anvil latch member (82) to resiliently rotate clockwise, thus enabling upper finger (88) of anvil latch member (82) to capture anvil pin (70) and thereby releasably couple together the proximal ends of stapler halves (12, 14), as seen in FIG. 5B. As shown in FIG. 5C, and with clamp lever (40) remaining in the open position, anvil half (14) is rotated toward anvil half (14) about proximal anvil pin (70) so that distal latch pin (68) of anvil half (14) is received into vertical slots (24) of cartridge channel side flanges (22) and jaw slots (50) of clamp lever (40). Distal jaw portions (20, 64) of stapler halves (12, 14) are now in a partially approximated state such that tissue received therebetween may be finally adjusted before clamping.

Figure 5D:
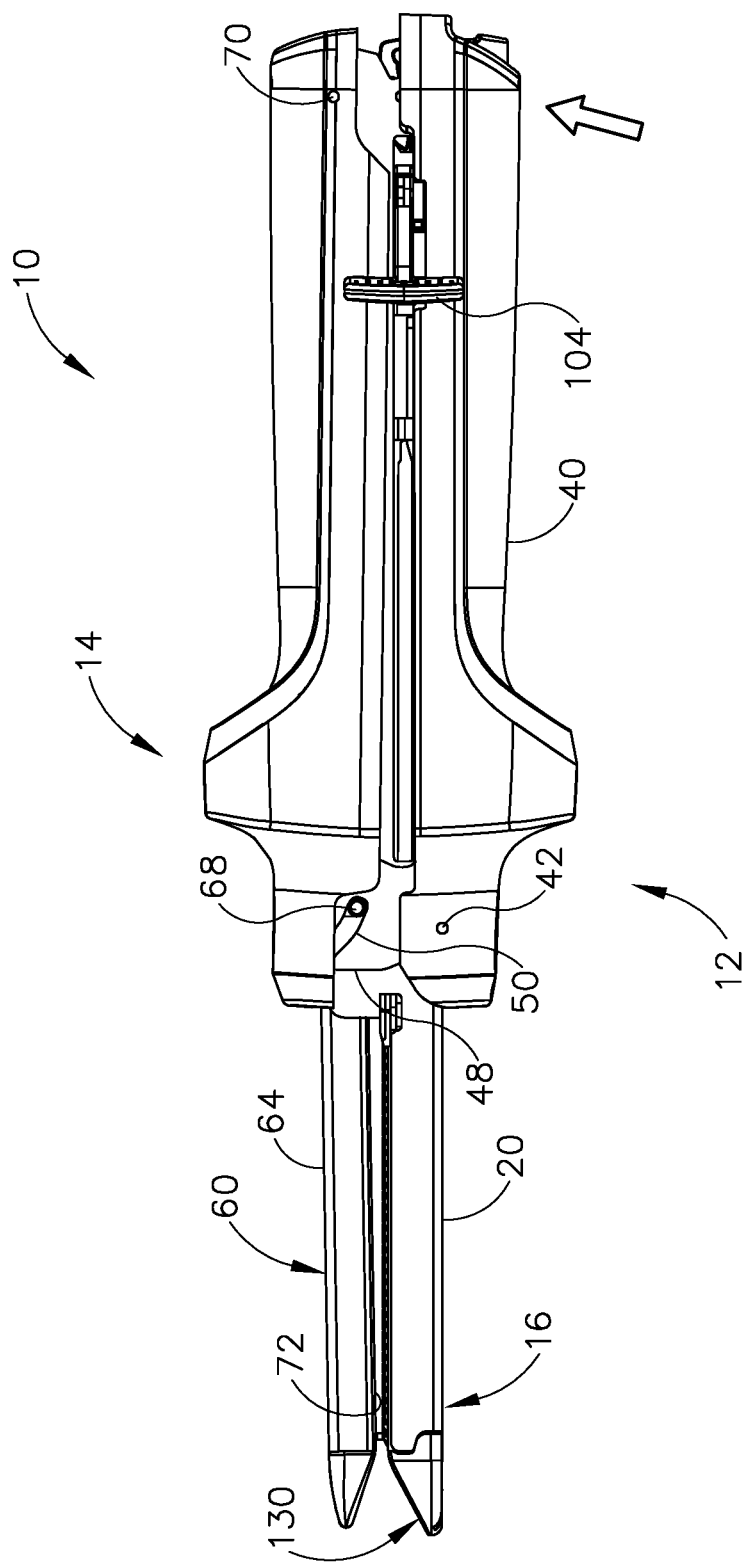
FIG. 5D depicts a side elevational view of the linear surgical stapler of FIG. 1, showing closure of the clamp lever to fully clamp the stapler halves together.
Figure 6:
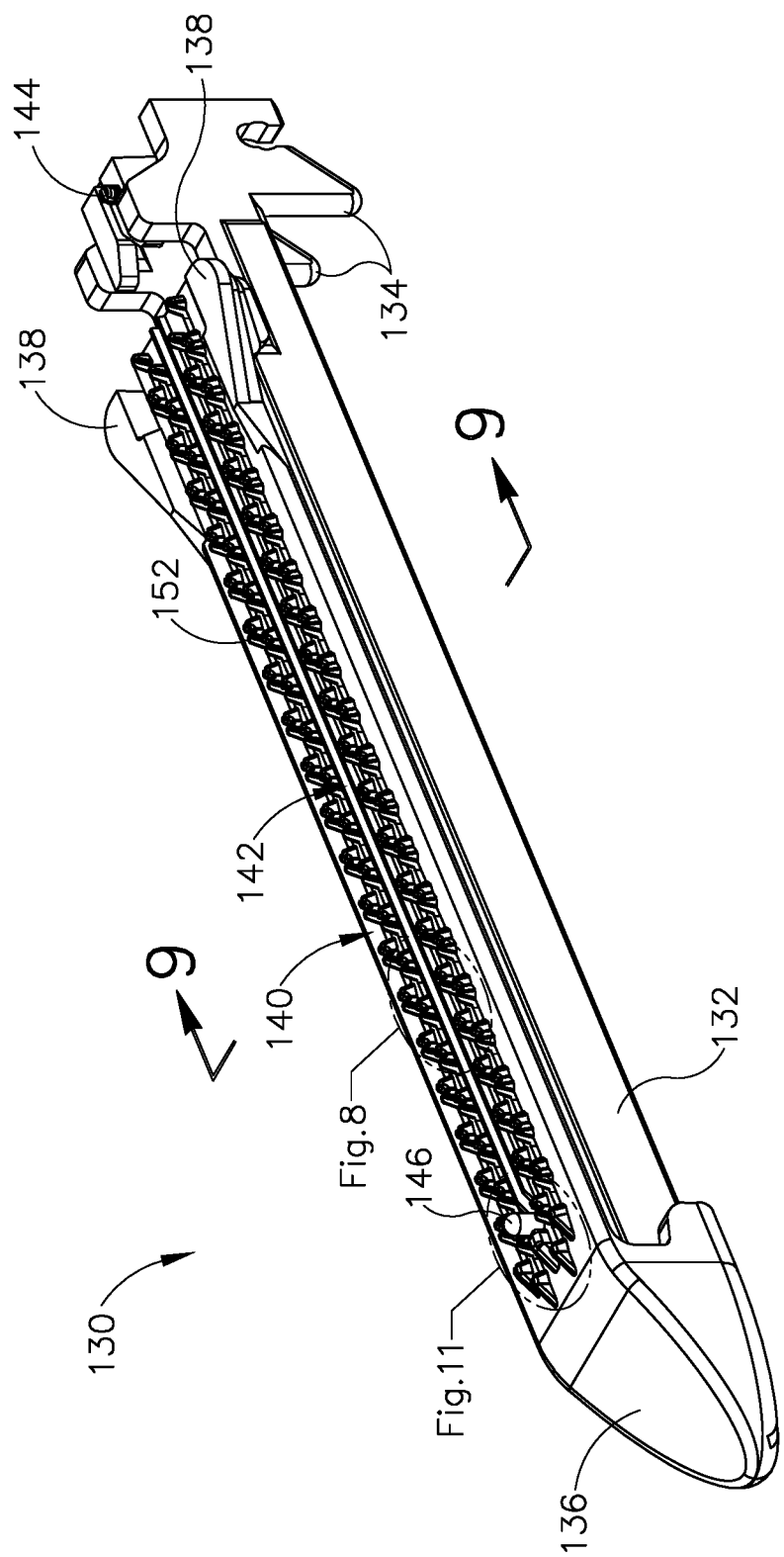
FIG. 6 shows a perspective view of an exemplary staple cartridge configured for use with the linear surgical stapler of FIG. 1.

As shown in FIG. 5D, clamp lever (40) is closed to draw anvil latch pin (68) against the closed proximal ends of jaw slots (50) and thereby fully clamp anvil half (14) against cartridge half (12), with tissue (not shown) clamped between staple cartridge (130) and anvil plate (72). A slight transverse gap is defined between staple cartridge (130) and anvil plate (72) by a tissue gap post (146) of staple cartridge (130) (see FIG. 6), thus accommodating the tissue therebetween with a predetermined degree of tissue compression. As shown in FIG. 6, tissue gap post (146) is disposed at a distal end of staple cartridge (130) and is configured to contact a distal end of anvil plate (72) when stapler (10) is in the fully clamped state shown in FIG. 5D.

Figure 5E:
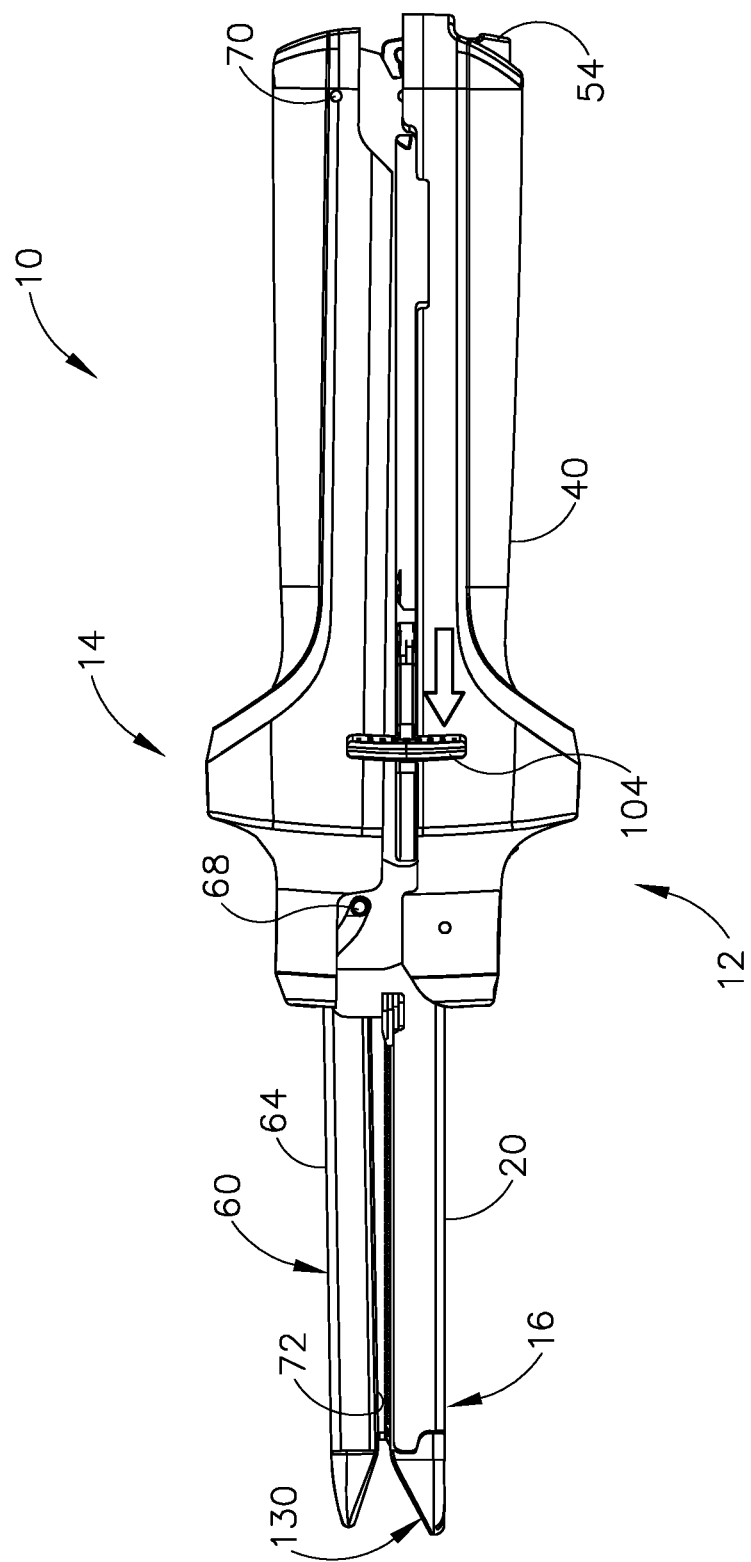
FIG. 5E depicts a side elevational view of the linear surgical stapler of FIG. 1, showing distal actuation of the firing assembly while the stapler halves are in the fully clamped state.

As shown in FIG. 5E, upon reaching the fully clamped state, stapler (10) may be fired by driving a deployed actuator (104, 106) of firing assembly (100) distally along proximal frame portion (18) of cartridge half (12). As described above in connection with FIG. 4, this action causes elongate beams (108, 112) of firing assembly (100) to translate distally through corresponding channels formed in staple cartridge (130) and thereby fire staples into the clamped tissue via cam ramps (110) and staple drivers (180), and simultaneously cut the clamped tissue with knife member (116). Following completion of the firing stroke, firing assembly (100) is returned to its proximal home position via the actuator (104, 106). Clamp lever latch member (54) may then be depressed to release the proximal end of clamp lever (40) from cartridge channel (16), thus permitting clamp lever (40) to be re-opened. Then, release button (90) of retaining assembly (80) may be depressed to release anvil half (14) from cartridge half (12) so that stapler halves (12, 14) may be separated from one another, thereby releasing the newly stapled and severed tissue. It will be understood that in some versions, stapler (10) may include features that promote decoupling of stapler halves (12, 14) similar to those features disclosed in U.S. patent application Ser. No. 16/165,587, issued as U.S. Pat. No. 11,033,266 on Jun. 15, 2021, incorporated by reference above.

II. Exemplary Staple Cartridge Having Staple Drivers and Tissue Grip Features that Promote Proper Formation of Three-Dimensional Staples As described below in connection with FIGS. 15-16, staple cartridge (130) of linear surgical stapler (10) is configured to apply staples (170) having a three-dimensional ("3D") formed configuration in which legs of each staple (170) are formed such that the leg tips are laterally offset from one another, thus providing the formed staple (170) with a non-planar shape. Such a staple configuration advantageously provides enhanced hemostasis and even distribution of compression forces along the resulting staple line applied to the patient tissue. Additionally, staple cartridge (130) is provided with stand-off members (152, 160, 162, 164) to enhance the ability of staple cartridge (130) to effectively grip tissue clamped between staple cartridge (130) and anvil plate (72) during the stapling and cutting steps described above. Accordingly, it may be desirable to suitably shape certain features of staple cartridge (130) to provide proper clearances to promote proper 3D formation of staples (170) and avoid staple malformation. Provision of such clearances also advantageously reduces the user input force required to actuate firing assembly (100) distally to fire staple cartridge (130).

It will be understood that while the features shown and described below are presented in the context of staple cartridge (130) for linear surgical stapler (10), such features may also be applied to staple cartridges configured for use with various other types of surgical staplers.

A. Overview of Exemplary Staple Cartridge

Figure 7:
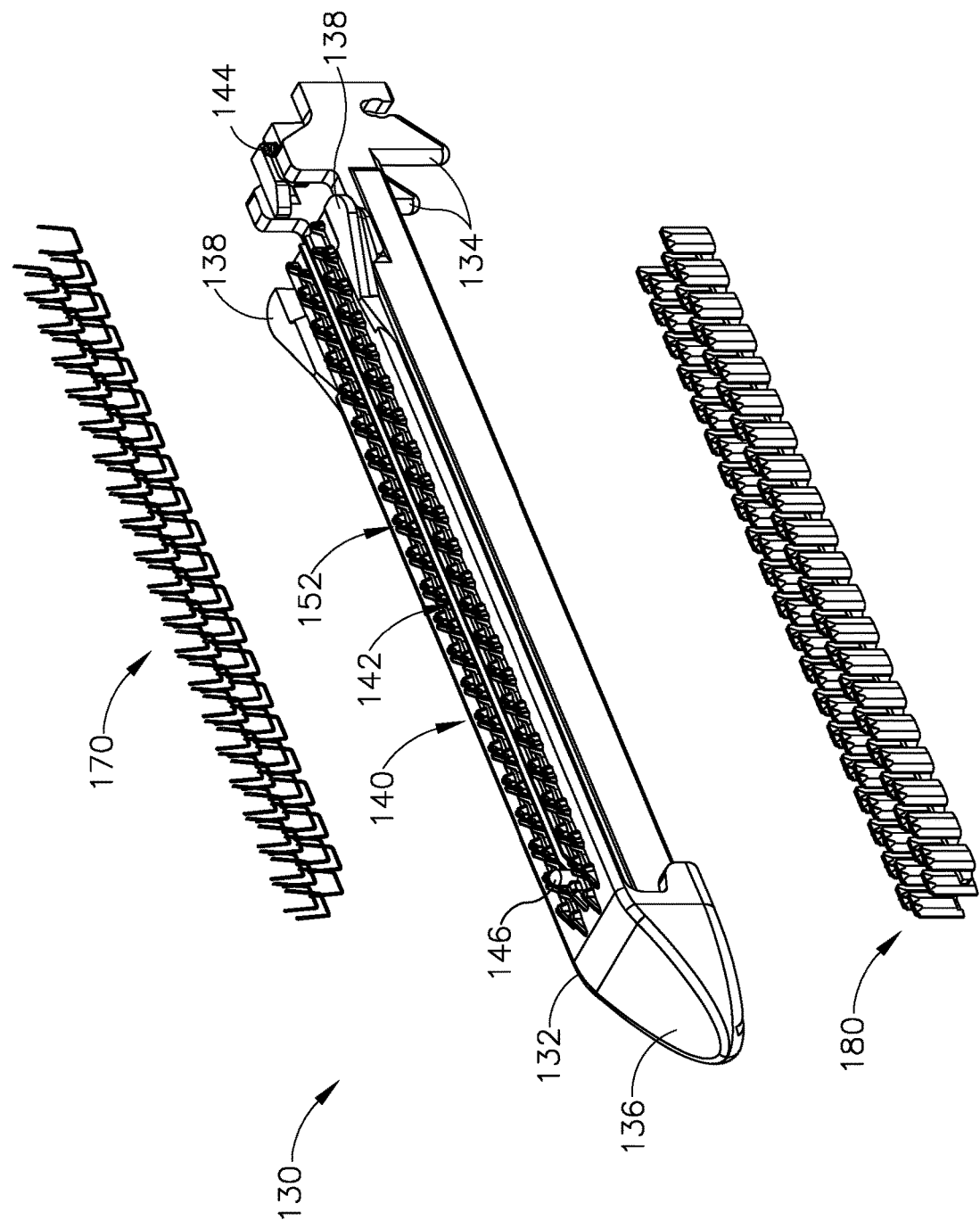
FIG. 7 depicts an exploded perspective view of the staple cartridge of FIG. 6.

As shown in FIGS. 6 and 7, staple cartridge (130) includes an elongate cartridge body (132), and a plurality of staples (170) and staple drivers (180) housed within cartridge body (132) beneath staples (170). A lockout bypass feature in the form of a swing tab (144) is rotatably coupled to a proximal end of cartridge body (132) and is described in greater detail below. In some versions, staple cartridge (130) may further include a bottom tray (not shown) that extends along an underside of cartridge body (132) and facilitates retention of staples (170) and staple drivers (180) within cartridge body (132).

Figure 12:
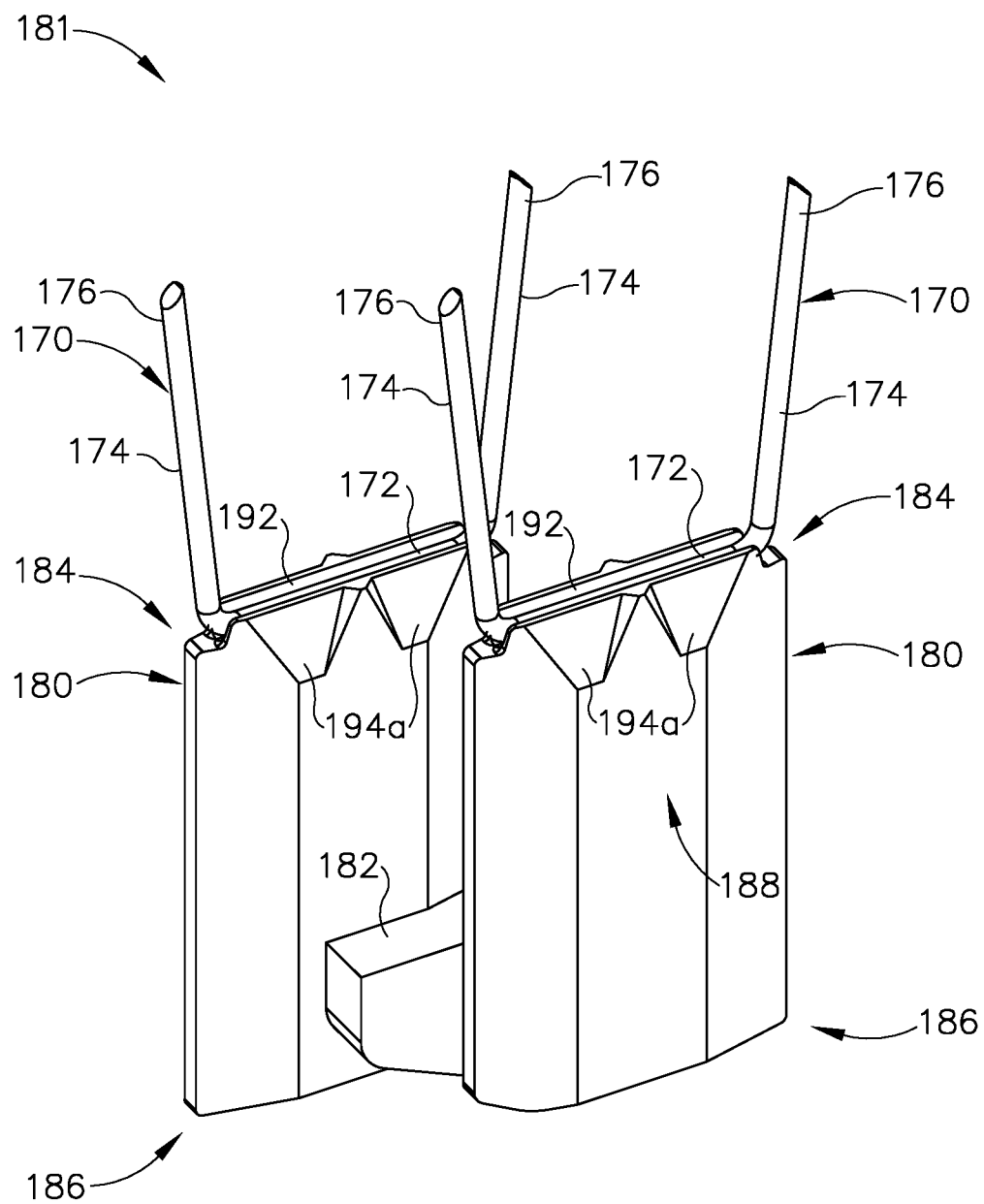
FIG. 12 depicts a perspective view of an exemplary pair of staple drivers and respective staples of the staple cartridge of FIG. 6.
Figure 15:
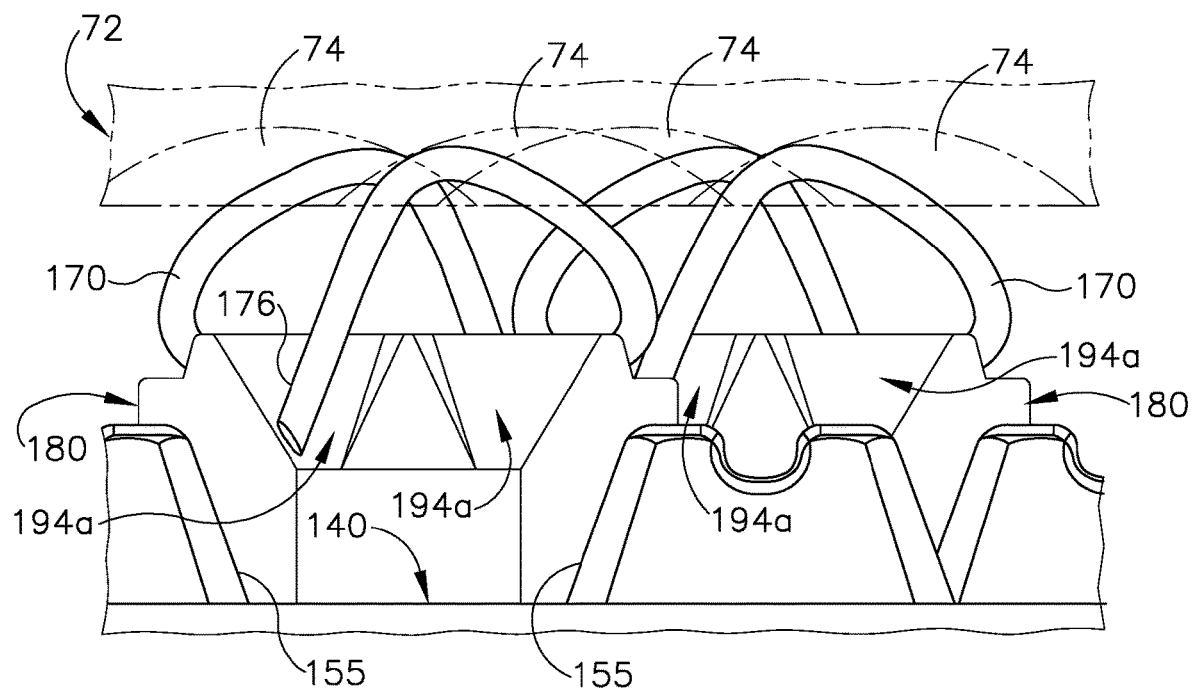
FIG. 15 depicts a side elevational view of a portion of the staple cartridge of FIG. 6 and a confronting portion of an anvil surface of the anvil half of the surgical stapler of FIG. 1, showing the stapler portions cooperating to form a pair of staples.
Figure 16:
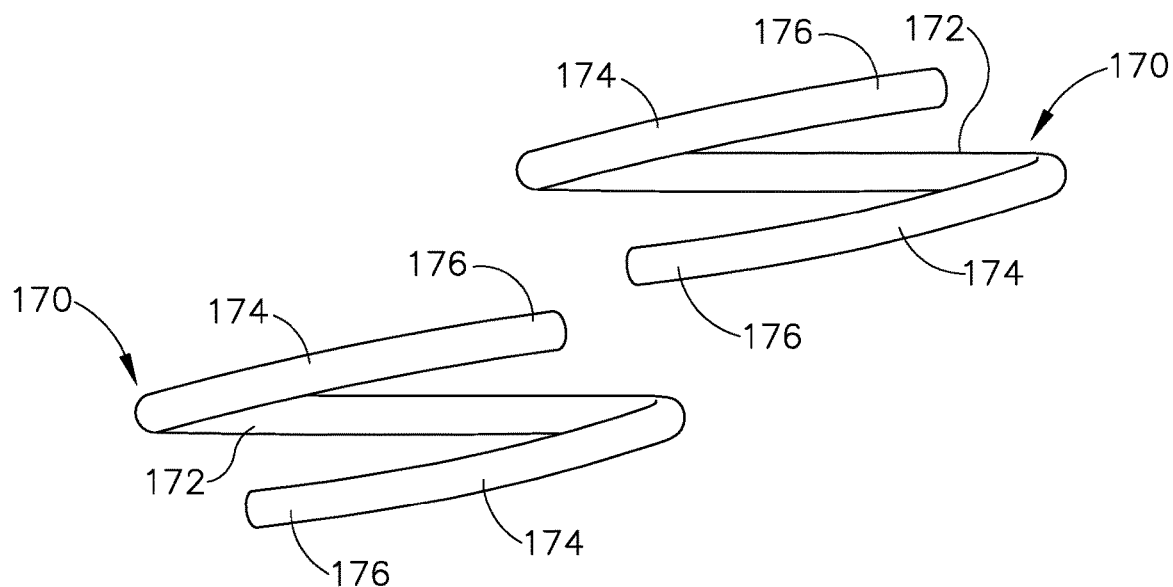
FIG. 16 depicts a top plan view of the pair of staples of FIG. 15 in a formed state.

Referring briefly to FIG. 12, each staple (170) includes a central crown (172) and a pair of legs (174) extending away from crown (172) and having leg tips (176). In the unformed state of staple (170), crown (172) and legs (174) form a U-like shape in which the leg tips (176) extend away from crown (172), and crown (172) and legs (174) reside in a common plane such that unformed staple (170) has a 2-dimensional shape. Referring briefly to FIGS. 15 and 16, in the 3D formed state of staple (170), each leg (174) has been bent by a respective staple forming pocket (74) of anvil plate (72) such that the leg tips (176) extend toward crown (172). More specifically, as shown in FIG. 16, each formed leg tip (176) is laterally offset from one another and from crown (172) on opposed sides of crown (172), thus providing formed staple (170) with a 3-dimensional shape having the functional benefits described above.

Returning to FIGS. 6 and 7, cartridge body (132) of the present example extends linearly along a longitudinal axis between a proximal end having a pair of hooks (134) and a distal end having a tapered nose (136). Proximal hooks (134) are configured to releasably capture clamp lever pivot pin (42) and extend downwardly through corresponding openings formed in a floor of cartridge channel (16) when staple cartridge (130) is seated within distal jaw portion (20) of cartridge channel (16). A pair of wing tabs (138) disposed on the lateral sides of cartridge body (132) near the proximal end are configured to facilitate insertion and removal of staple cartridge (130) relative to distal jaw portion (20).

As shown best in FIGS. 6-9, an upper side of cartridge body (132) defines a deck (140). An elongate knife slot (142) extends longitudinally through deck (140) along the longitudinal axis of staple cartridge (130) and is configured to slidably receive knife member (116) of firing assembly (100) therethrough in response to distal actuation thereof, described above. A firing lockout bypass feature in the form of a swing tab (144) is rotatably coupled to cartridge body (132) at a proximal end of knife slot (142). Swing tab (144) is configured to rotate between a deployed position in which swing tab (144) extends perpendicularly across the proximal end of knife slot (142), and a retracted position in which swing tab (144) extends parallel to knife slot (142). As shown and described below in connection with FIGS. 27A-27B, swing tab (144) in the deployed position is configured to urge firing assembly (100) from a lockout state toward a firing state in which firing beams (108, 112) may translate distally through staple cartridge (130) to enact stapling and cutting of tissue clamped by stapler (10).

A rigid tissue gap post (146) is secured at a distal end of knife slot (142) and protrudes upwardly away from cartridge deck (140). A rounded upper end of tissue gap post (146) is configured to contact a distal end of anvil plate (72) and thereby define a tissue gap between cartridge deck (140) and anvil plate (72) when stapler halves (12, 14) are clamped together in the manner described above.

Figure 11:
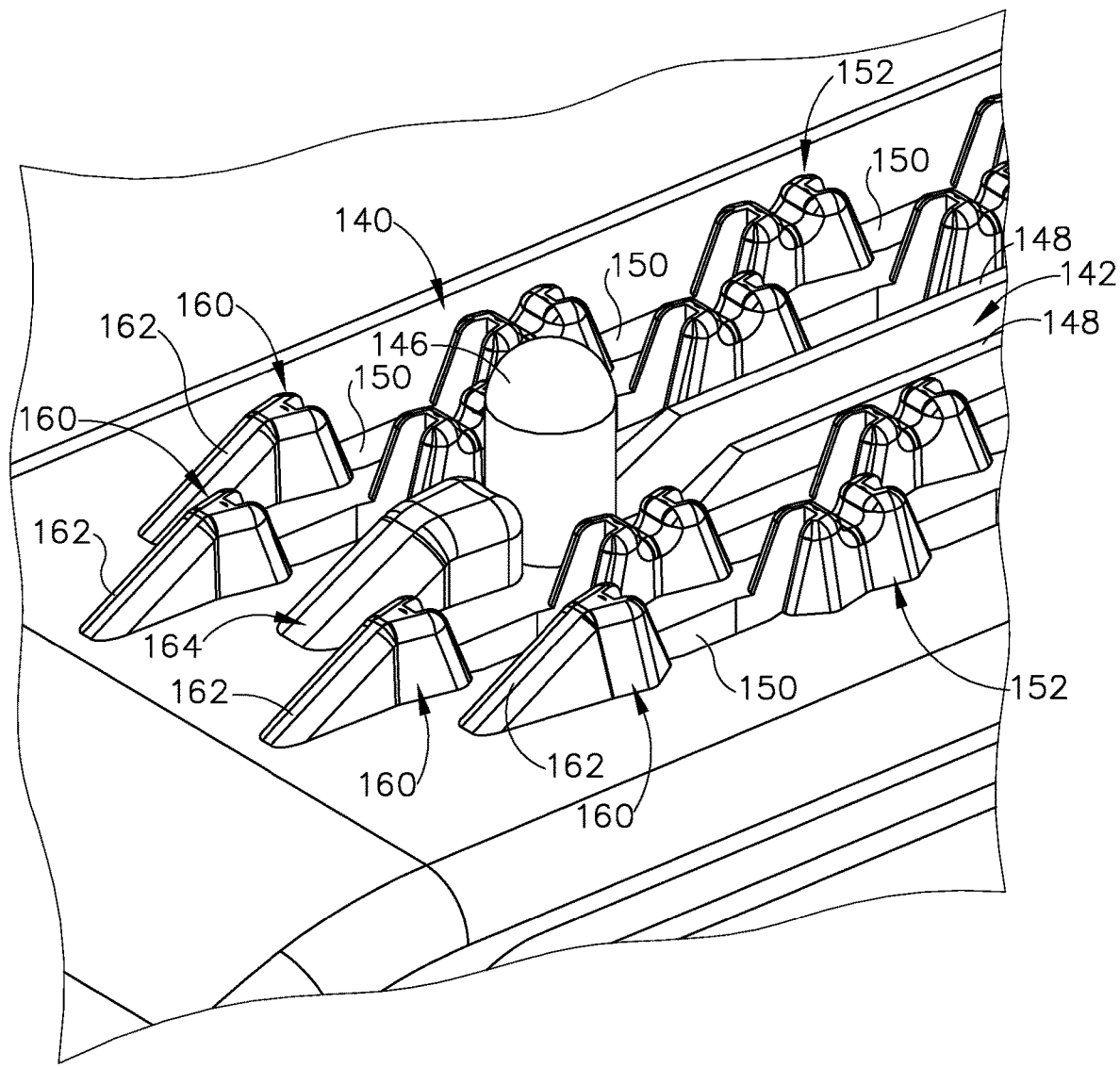
FIG. 11 depicts an enlarged perspective view of tissue gripping features disposed at a distal end of the deck surface of the staple cartridge of FIG. 6.

A pair of elongate ribs (148) extend along opposing sides of knife slot (142) and elongate ribs (148), and project away from deck (140) to define raised surfaces. Elongate ribs (148) terminate at proximal and distal ends of knife slot (142) and are configured to promote enhanced gripping of tissue along knife slot (142), thus stabilizing the tissue during cutting by knife member (116). As shown in FIG. 11, elongate ribs (148) of the present version have tapered distal ends disposed proximal to tissue gap post (146).

Cartridge body (132) of staple cartridge (130) further includes a plurality of staple openings (150) that extend transversely through cartridge body (132) and open to deck (140). In the present example, staple openings (150) are arranged in first and second parallel rows along each side of knife slot (142), such that the staple openings (150) of each row are longitudinally staggered relative to staple openings (150) of the adjacent row. It will be understood that various suitable arrangements and quantities of staple openings (150) may be provided in other versions of staple cartridge (130). Each staple opening (150) is configured to house a respective staple driver (180) and staple (170) therein. As described above, cam ramps (110) of firing assembly are configured to engage the undersides of staple drivers (180) and actuate staple drivers (180) upwardly within staple openings (150) to thereby drive (or "fire") staples (170) from staple openings (150), into tissue, and against anvil plate (72).

As shown best in FIGS. 8-11, staple cartridge (130) further includes a plurality of tissue gripping members in form of stand-off members (152, 160, 162, 164) that are arranged on and project upwardly from cartridge deck (140). Stand-off members (152, 160, 162, 164) are distributed along a length of deck (140) and are laterally offset from knife slot (142) and elongate ribs (148) to align with and open to a respective one or more staple openings (150). As described below, stand-off members (152, 160, 162, 164) are configured to grip and thereby stabilize tissue when deck (140) and anvil plate (72) are clamped together; and, moreover, optimize tissue compression at the staple locations to facilitate effective stapling and cutting of the tissue. While stand-off members (152, 160, 162, 164) are formed integrally with cartridge body (132) in the present version, it will be understood that stand-off members (152, 160, 162, 164) may be formed separately from and coupled to cartridge body (132) in other versions.

Figure 8:
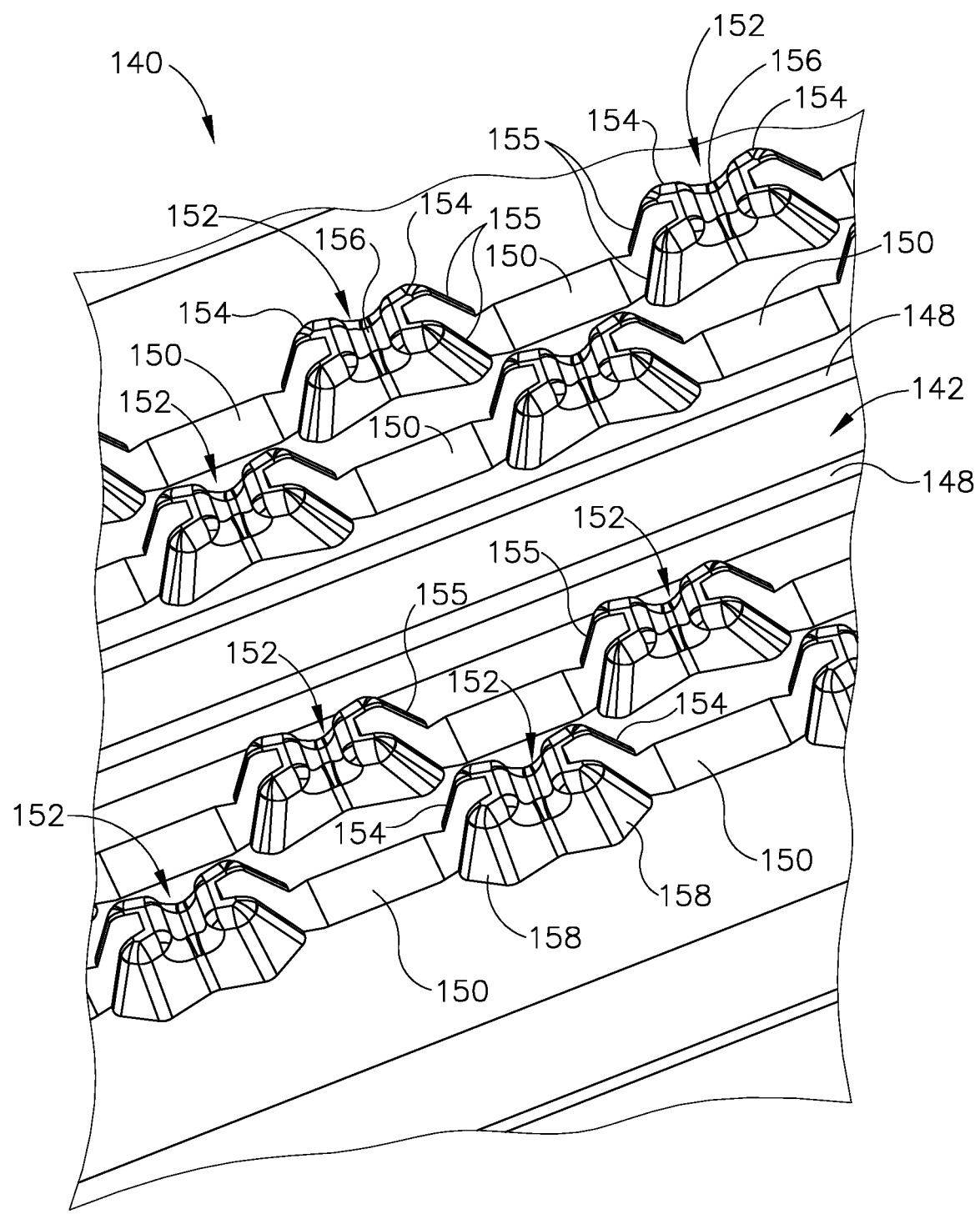
FIG. 8 depicts an enlarged perspective view of the staple cartridge of FIG. 6, showing tissue gripping features disposed along a length of a deck surface of the staple cartridge.
Figure 9:
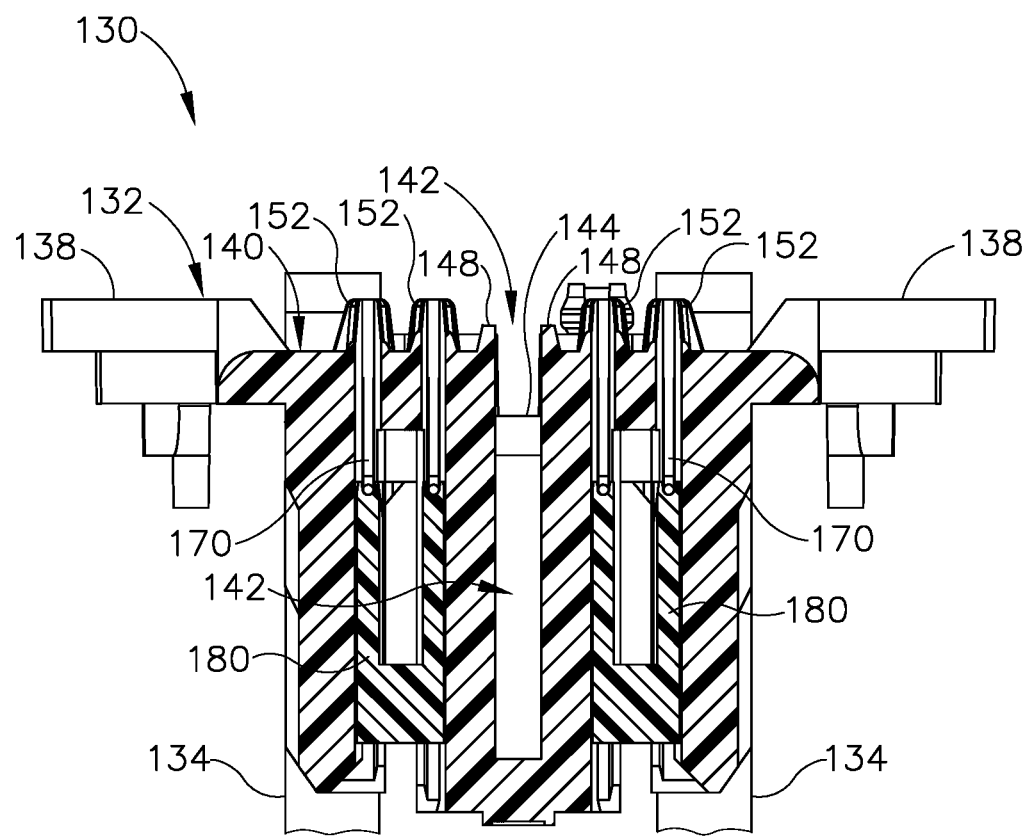
FIG. 9 depicts a sectional end view of the staple cartridge of FIG. 6, taken along section line 9-9 in FIG. 6.
Figure 10:
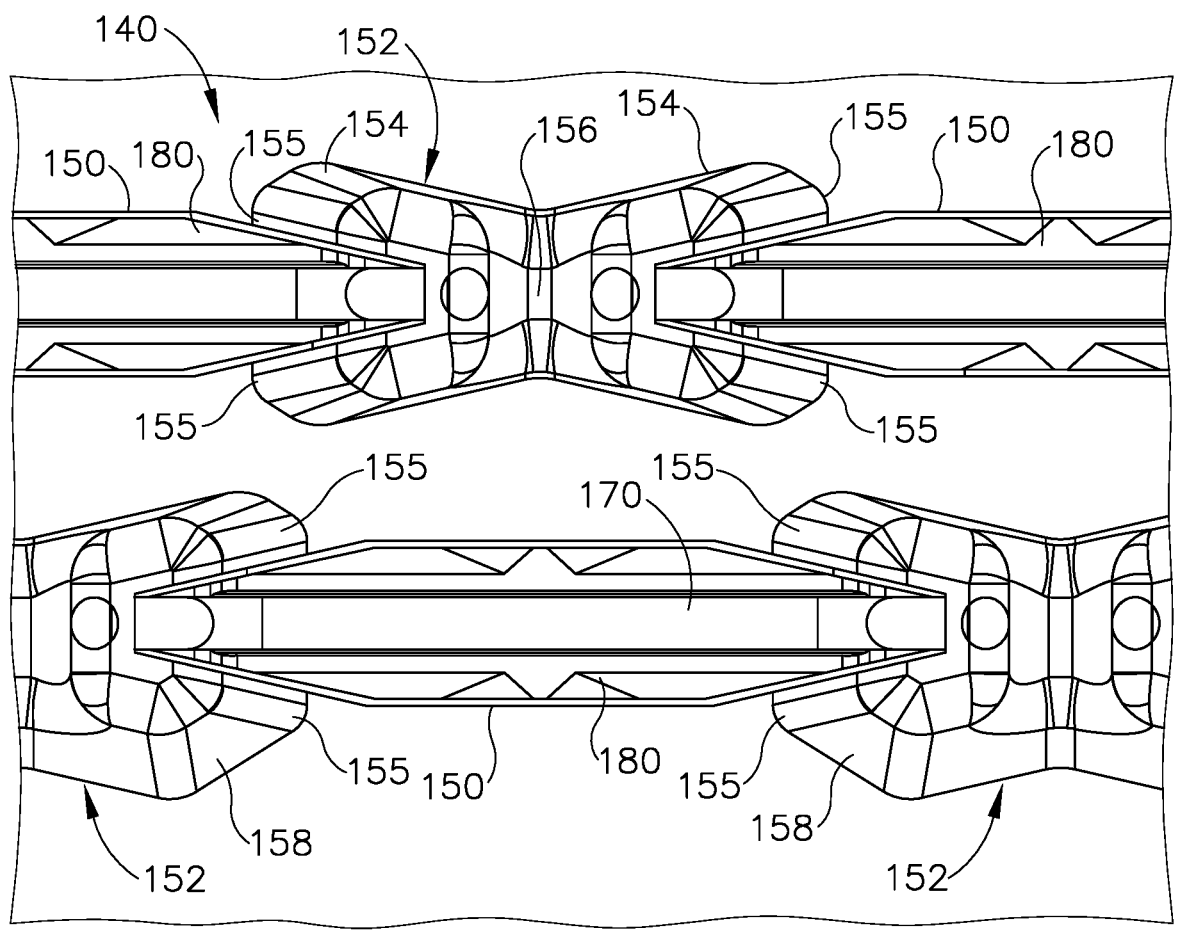
FIG. 10 depicts an enlarged top plan view of tissue gripping features disposed on the deck surface of the staple cartridge of FIG. 6.

As shown in FIGS. 8-10, a first group of stand-off members on cartridge deck (140) is shown in the form of cleats (152) arranged discretely along the length of knife slot (142) in alignment with staple openings (150). Each cleat (152) includes a pair of end features (154) that face in opposing longitudinal directions. In particular, a first end feature (154) opens to and wraps partially around an end portion of a first staple opening (150) within a given row of staple openings (150), and an opposed second end feature (154) opens to and wraps partially around an end portion of an adjacent second staple opening (150) within the same row of staple openings (150). First and second end features (154) are integrally connected by a recessed bridge feature (156).

Each end feature (154) of a cleat (152) has a generally U-shaped cross-section in a plane that extends parallel to deck (140), along the height of cleat (152). Each end feature (154) also defines an inner wall that joins with and protrudes outwardly from an inner wall of the respective staple opening (150). In this manner, each end feature (154) opens to and communicates with a respective staple opening (150). Accordingly, each end feature (154) is configured to guide a respective staple leg (174) of a corresponding staple (170) (see FIG. 12), as well as the respective staple driver (180), as the staple (170) is ejected upwardly from the staple opening (150) by the staple driver (180). Each end feature (154) thus cooperates with a confronting end feature (154) of an adjacent cleat (152), or with an endcap (160) (see FIG. 11) described below, to provide such guidance of staples (170) and staple drivers (180).

As shown best in FIGS. 8 and 10, each end feature (154) of a cleat (152) tapers toward the respective recessed bridge feature (156) along a height of cleat (152) in a direction away from deck (140), thus providing each cleat (152) with a trapezoidal-shaped side profile. In that regard, as shown best in FIG. 10, each end feature (154) includes an angled end surface (155) that slopes toward recessed bridge feature (156) and is rounded along a height thereof. This rounded configuration of angled end surfaces (155) enables each end feature (154) to confront the respective staple leg (174) and respective staple driver (180) to thereby effectively guide the staple (170) and staple driver (180) upwardly, while also providing effective clearance to promote proper 3D formation of the staple leg (174). In particular, the rounded configuration of angled end surfaces (155) mitigates the risk of a tip of staple leg (174) striking an end feature (154) when the staple leg (174) is being formed by anvil plate (72), which might otherwise induce malformation of the staple leg (174).

As shown in FIGS. 8 and 10, the laterally outermost rows of cleats (152) on cartridge deck (140) of the present example are formed with outer sides having planar faces (158) that are angled relative to a length of staple cartridge (130). Accordingly, these particular cleats (152) are asymmetrical about their longitudinal axes, which may help to facilitate a molding process for forming cartridge body (132).

While cleats (152) of the present example are discretely formed relative to one another such that each cleat (152) is freestanding and spaced apart from adjacent cleats (152), in other versions cleats (152) may be interconnected with one another along one or more portions of cartridge deck (140).

As shown in FIG. 11, cartridge deck (140) includes additional stand-off members in the form of proximally facing endcaps (160) disposed at the distal ends of the rows of staple openings (150). In the present version, a proximal portion of each endcap (160) is similar in shape to cleat end features (154) described above. In particular, the proximal portion of each endcap (160) has a U-shape and wraps partially around a distal end portion of a respective staple opening (150). Accordingly, each endcap (160) cooperates with a confronting end feature (154) of an adjacent cleat (152) within the same row to guide a respective staple (170) and staple driver (180) during firing of staple cartridge (130). In the present example, each endcap (160) further includes a distal ramp feature (162) that tapers distally toward cartridge nose (136). A similar ramp feature (164) is positioned distally of and in longitudinal alignment with tissue gap post (146). Ramp features (162, 164) are configured to promote smooth insertion of the distal end of cartridge half (12) of stapler (10) into or underneath a tissue structure without the tissue snagging on or otherwise bunching against cleats (152), endcaps (160), or tissue gap post (146).

In the present example, stand-off members (152, 160, 162, 164) protrude from cartridge deck (140) with a uniform maximum height and thus collectively define a raised tissue engagement plane. In other versions, stand-off members (152, 160, 162, 164) may protrude from cartridge deck (140) with varying heights and thus define two or more raised tissue engagement planes.

Figure 13:
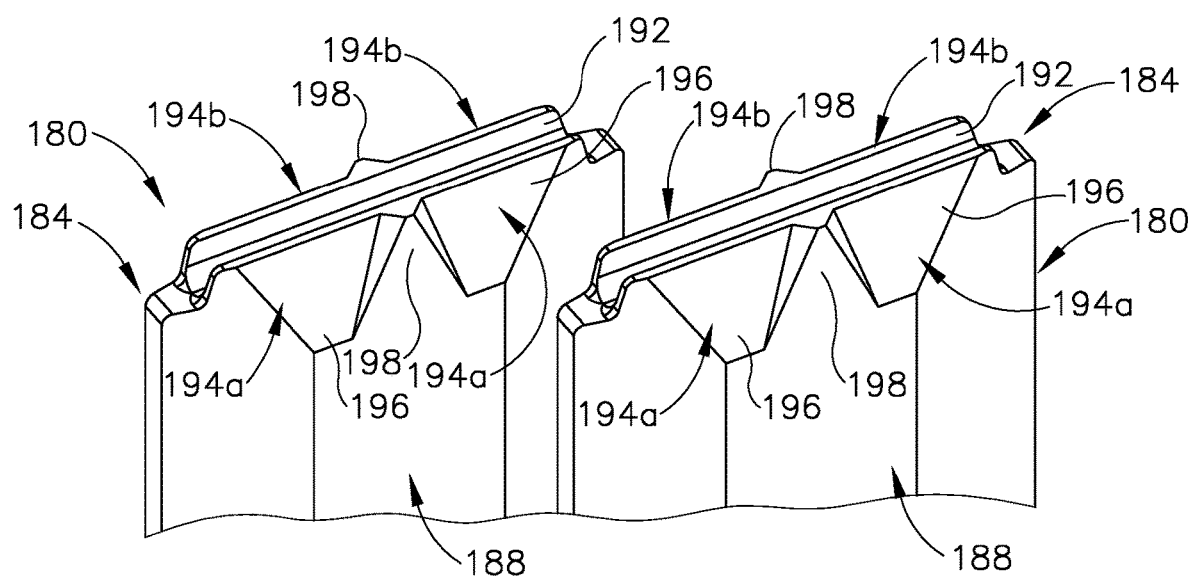
FIG. 13 depicts an enlarged perspective view of a top portion of the staple drivers of FIG. 12.
Figure 14:
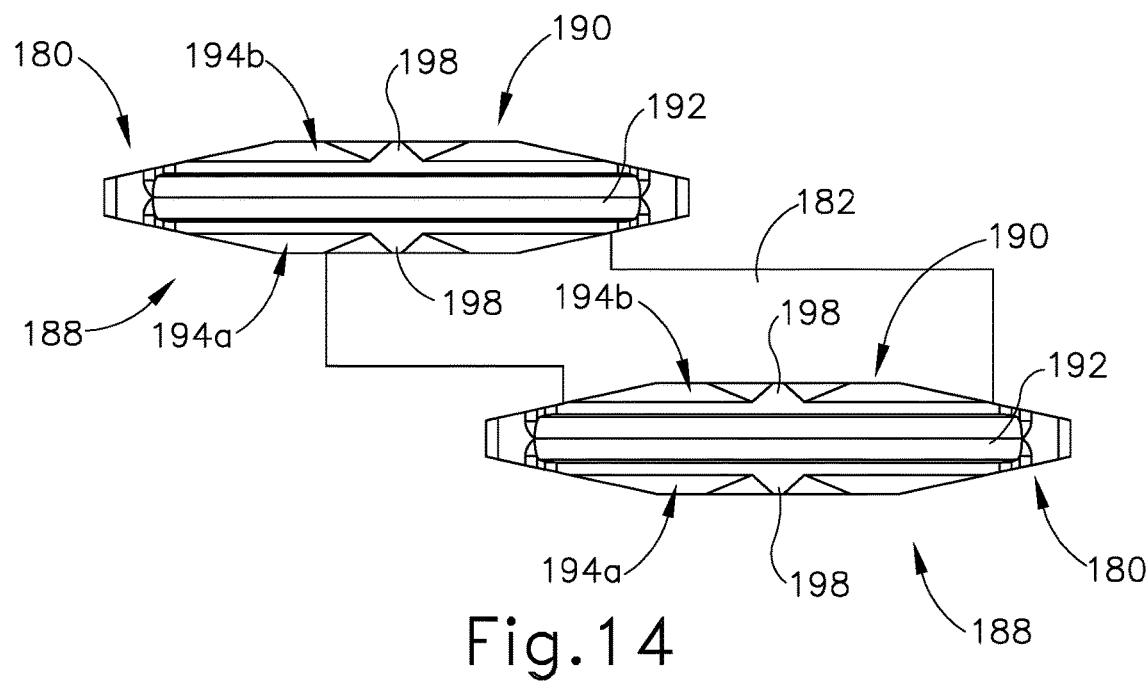
FIG. 14 depicts a top plan view of the staple drivers of FIG. 12.

FIGS. 12-14 show details of an exemplary pair of staple drivers (180) of staple cartridge (130). In the present example, each pair of staple drivers (180) is integrally formed as a driver unit (181) having a bridge element (182) that interconnects staple drivers (180) at their lower ends (186). Staple drivers (180) of driver unit (181) are arranged in a staggered formation in which staple drivers (180) are laterally and longitudinally offset from one another, relative to the longitudinal axis of staple cartridge (130), such that staple drivers (180) are configured to align with respective staple openings (150) of cartridge body (132). As shown in FIG. 12, each staple driver (180) includes an upper end (184), a lower end (186), a first exterior lateral side (188), and an opposed second exterior lateral side (190). As seen in FIG. 14, staple driver (180) of the present example is formed along its height with a transverse cross-section having an elongate octagonal shape that defines first and second lateral sides (188, 190). Upper end (184) of staple driver (180) includes a groove (192) configured to receive and support the crown (172) of a respective staple (170).

Each staple driver (180) of the present example is thrilled with staple leg receiving features in the form of pockets (194a, 194b) that open to upper end (184) and are configured to receive staple leg tips (176) during formation of staple legs (174) by anvil plate (72) when stapler (10) is fired. In particular, first lateral side (188) of driver (180) includes a first pair of adjacent pocket (194a) at upper end (184), and second lateral side (190) includes a second pair of adjacent pockets (194h) at upper end (184). In the present version, pockets (194a, 194b) are shaped uniformly and are arranged symmetrically such that each pocket (194a) of first lateral side (188) is aligned with an opposed pocket (194b) of second lateral side (190).

Each pocket (194a, 194b) of a staple driver (180) is defined by a respective chamfered surface (196) at upper end (184) and is separated from the adjacent pocket (194a, 194b) of the same lateral side (188, 190) by a boss (198) that is centrally positioned on the respective lateral side (188, 190). Each chamfered surface (196) is angled toward groove (192) such that pockets (194a, 194b) of first lateral side (188) and pockets (194a, 194b) of second lateral side (190) are angled toward one another at their upper ends. Each pocket (194a, 194b) tapers in width in a direction toward lower end (186), so as to have a generally trapezoidal shape. In contrast, each boss (198) tapers in width in a direction toward upper end (184), so as to have a generally triangular shape. Moreover, each boss (198) defines an inner sidewall of each corresponding pockets (194a, 194b) near a center of upper groove (192), whereas each pocket (194a, 194b) is open at an opposed side near a corresponding end of upper groove (192). Bosses (198) are configured to facilitate proper seating of a staple crown (172) within upper groove (192) during assembly of staple cartridge (130).

As shown in FIG. 15, each pocket (194a, 194b) of a staple driver (180) is configured to receive a staple leg tip (176) during formation of staples (170), such that each staple leg tip (176) confronts, though does not necessarily contact, a respective chamfered surface (196) of staple driver (180). Accordingly, and advantageously, provision of pockets (194a, 194b) in staple drivers (180), along with rounded angled end surfaces (155) of cleats (152) described above, enables proper 3D formation of staples (170) without staple legs (174) striking lateral sides of staple drivers (180), or end features (154) of cleats (152), in manners that might otherwise induce malformation of staples (170).

As shown in FIG. 15, a first leg tip (176) of a staple (170) is received within a pocket (194a) of first lateral side (188) of driver (180) during 3D staple formation. Similarly, a second leg tip (176) is received within a pocket (194b) of second lateral side (190) that is diagonally opposed from the first pocket (194a). Accordingly, the remaining pocket (194a) of first lateral side (188) and the diagonally opposed remaining pocket (194b) of second lateral side (190) are left unused in the present example. However, it will be understood that providing a pair of pockets (194a, 194b) on each lateral side (188, 190) of staple driver (180) enables staple drivers (180) to accommodate alternative configurations of staple forming pockets (74) of anvil plate (72) and resulting 3D formed configurations of staples (170). For instance, in some versions, at least some of the staple forming pockets (74) of anvil plate (72) may be alternatively configured to direct staple legs (174) into the unused pair of diagonally opposed pockets (194a, 194b) shown in FIG. 15. Accordingly, each staple driver (180) is thus configured to accommodate formation of a staple (170) having a 3D configuration that is mirrored relative to the 3D configuration shown in FIG. 16.

B. Exemplary Alternative Staple Driver of Staple Cartridge

Figure 20:
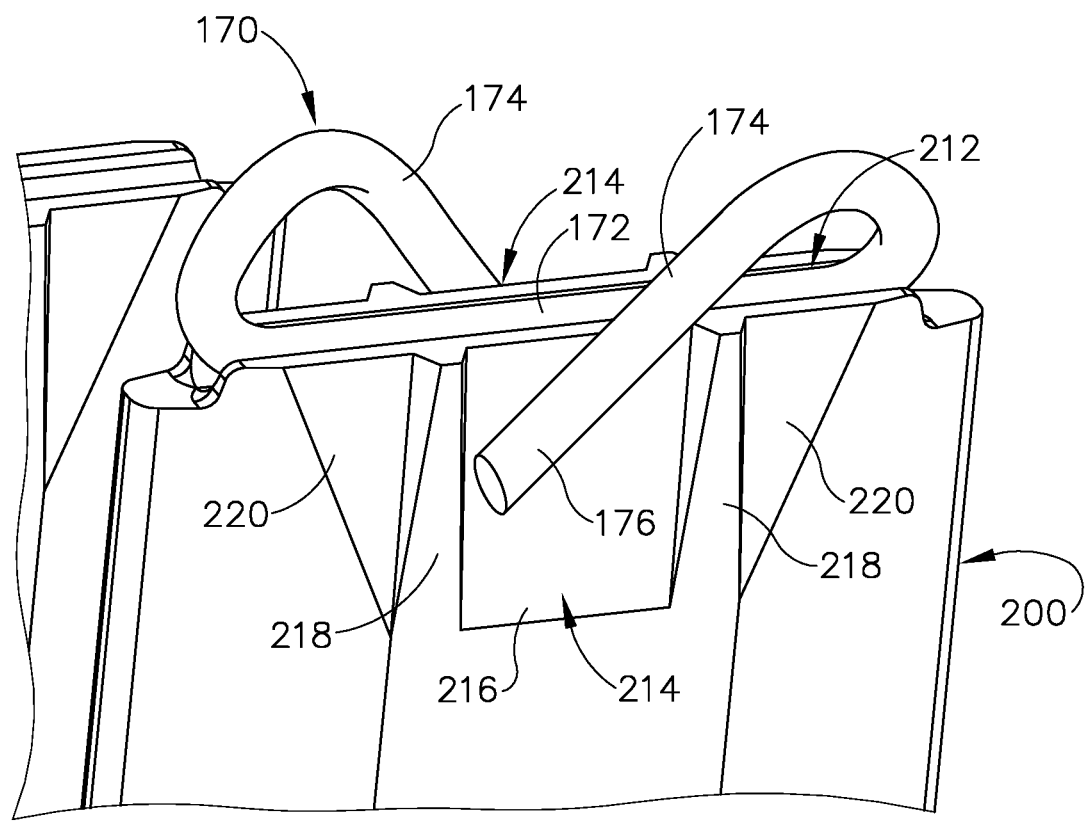
FIG. 20 depicts an enlarged perspective view of one of the staple drivers of FIG. 17 in combination with a staple formed by the staple driver in cooperation with an anvil pocket of the anvil half of the linear surgical stapler of FIG. 1.

It may be desirable to alternatively configure staple cartridge (130) in some applications to accommodate different thicknesses of patient tissue to be fired upon. For instance, cartridge deck (140) and stand-off members (152, 160, 162, 164) may be alternatively configured in dimension to accommodate stapling relatively thinner tissues, such as those of vascular structures, for example. In such alternative versions of staple cartridge (130), staples (170) may assume a slightly different 3D formed shape relative to the staple shape shown in FIG. 16. For instance, the staple legs (174) may be formed such that the formed staple (170) has a smaller formed height (e.g., approximately 0.035 inches to 0.040 inches), and such that leg tips (176) are positioned closer to a center of crown (172) than to the ends of crown (172), as shown in FIG. 20. Accordingly, pockets (194a, 194b) and bosses (198) of staple drivers (180) may warrant slight reconfiguring to accommodate such 3D formation differences of staples (170) without undesirable striking of staple legs (174) on features of staple drivers (180), which might otherwise yield staple malformation and resulting increases in user input force required to fire surgical stapler (10). Such an exemplary variation of staple drivers (180) is described in greater detail below.

Figure 17:
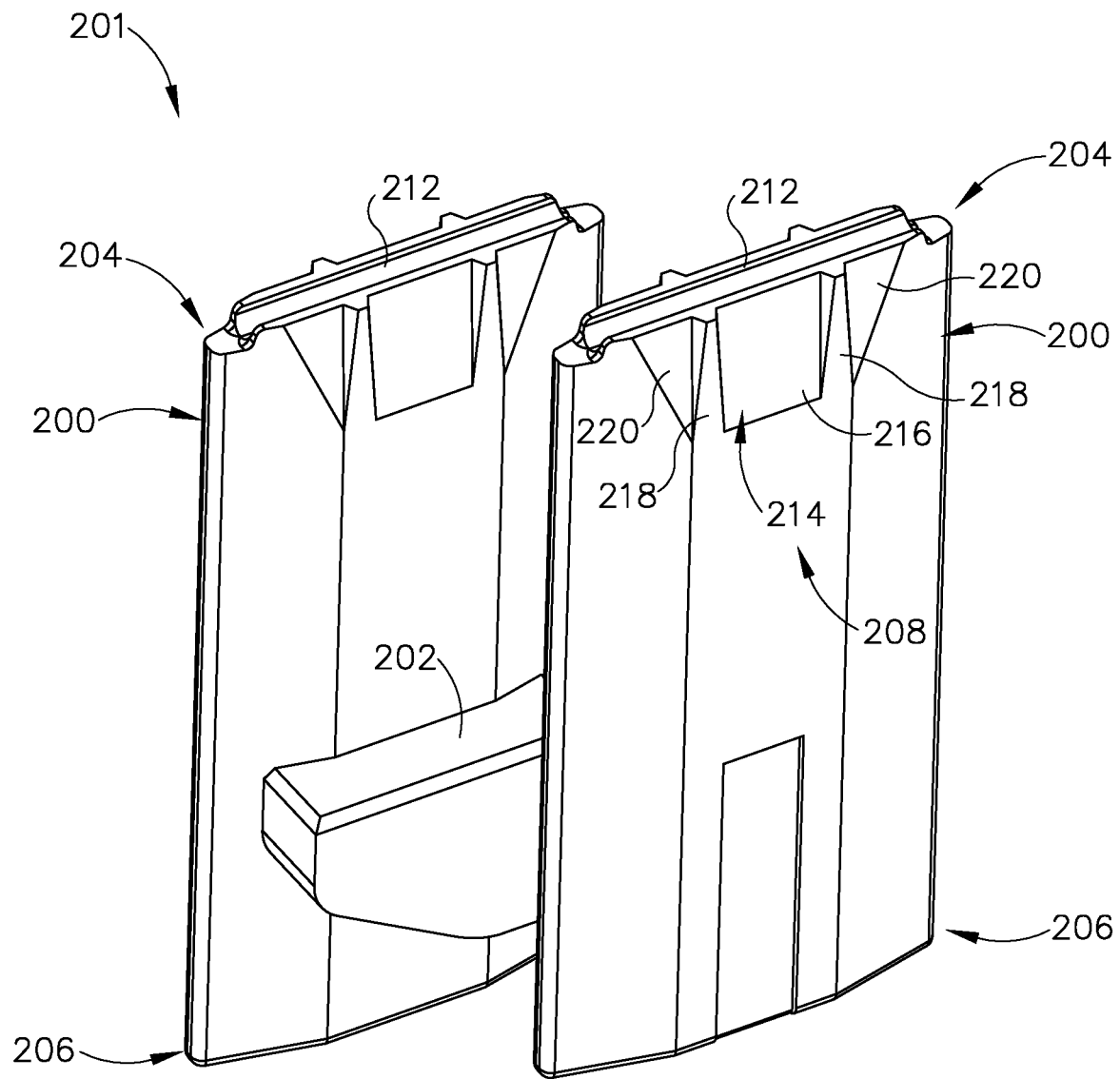
FIG. 17 depicts a perspective view of another exemplary pair of staple drivers configured for use with the staple cartridge of FIG. 6.
Figure 18:
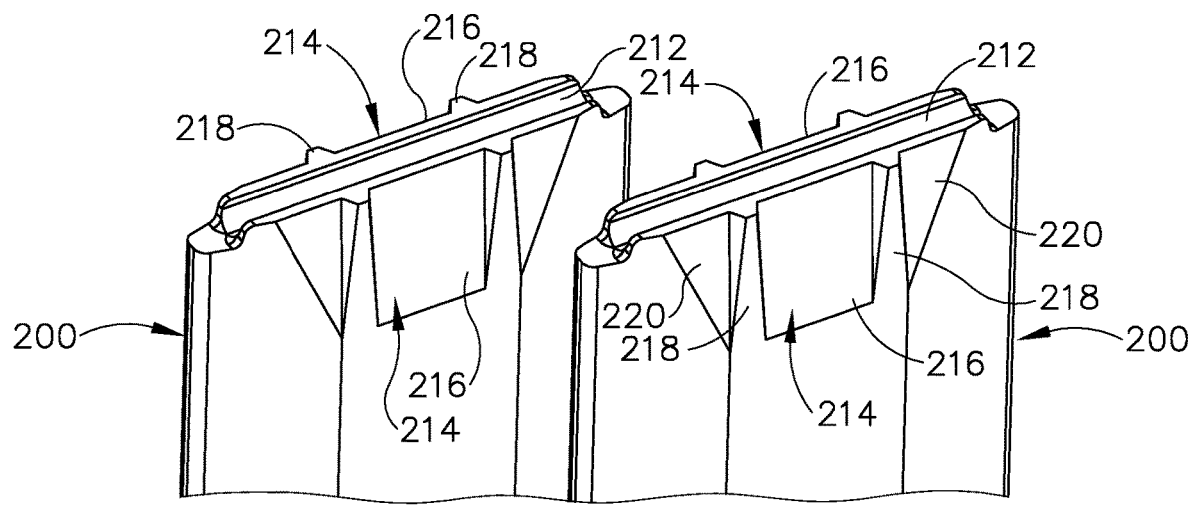
FIG. 18 depicts an enlarged perspective view of a top portion of the staple drivers of FIG. 17.
Figure 19:
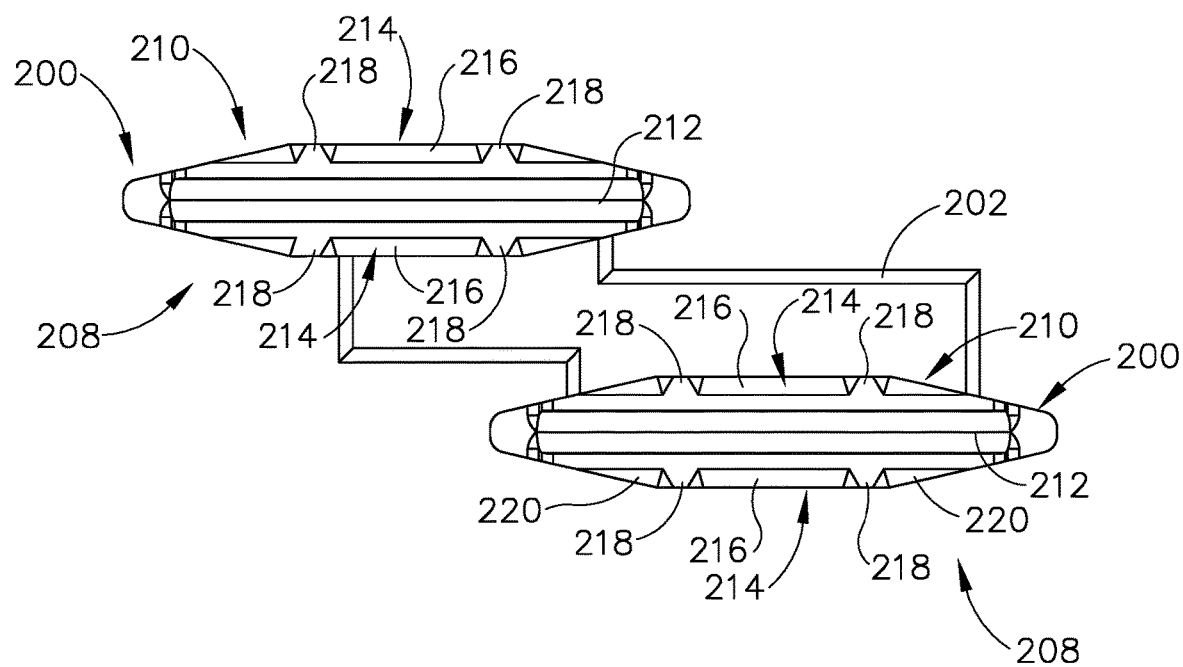
FIG. 19 depicts a top plan view of the staple drivers of FIG. 17

FIGS. 17-19 show an exemplary alternative pair of staple drivers (200) configured for use with staple cartridge (130). Staple drivers (200) are similar to staple drivers (180) described above except as otherwise described below. Similar to staple drivers (180), staple drivers (200) are integrally formed as a driver unit (201) having a bridge element (202) that interconnects staple drivers (200) at their lower ends (206) such that staple drivers (200) are arranged in a staggered configuration. Additionally, each staple driver (200) includes an upper end (204), a lower end (204), a first lateral side (208), an opposed second lateral side (210), a groove (212) at upper end (204), and an elongate octagonal shape transversely along its height.

Unlike staple drivers (180), each lateral side (208, 210) of staple driver (200) includes a single pocket (194) configured to receive a staple leg (174) during formation of staples (170). Each pocket (194) is centrally positioned relative to upper groove (212) and is defined by a respective chamfered surface (216) that is angled toward groove (212) at its upper end. Each chamfered surface (216) is bound on its two sides by a pair of bosses (218), with each boss (218) being offset equidistantly from a center of upper groove (212) along the span of groove (212). Each boss (218) defines a respective sidewall of the corresponding pocket (194), and bosses (218) are shaped to provide each chamfered surface (216) with a generally rectangular shape. Additionally, each boss (218) has chamfered side surfaces so as to be tapered along its height in a direction toward upper end (204). Each lateral side (208, 210) of staple driver (200) further includes a pair of side relief cuts defining triangular surfaces (220) that abut the outer sides of bosses (218) and are coplanar with the respective chamfered surface (216).

As shown in FIG. 20, each pocket (194) is configured to receive a respective leg tip (176) of a staple (170) during 3D formation thereof by staple forming pockets (74) of anvil plate (72). Similar to pockets (194a, 194b) of staple drivers (180), pockets (214) of staple driver (200) are configured to receive staple leg tips (176) such that leg tips (176) confront, but do not necessarily contact, chamfered surfaces (216). Accordingly, staple drivers (200) are thus configured to promote proper 3D formation of staples (170) in tissue, such as relatively thinner tissues for which a formed staple height of approximately 0.035 inches to 0.040 inches, for example, is desired.

III. Exemplary Features for Minimizing Plastic Deformation of Firing Lockout Spring of Linear Surgical Stapler As described above, firing assembly (100) of linear surgical stapler (10) is translatable distally within cartridge channel (16) from a proximal home position (see FIG. 5D) to a distal fired position (see FIG. 5E) to simultaneously staple and cut tissue clamped between the distal portions of stapler halves (12, 14). As described in greater detail below, cartridge half (12) further includes a resilient lockout member (250) in the form of a leaf spring configured to bias firing assembly (100) toward a lockout state in the absence of an unfired (or "unspent") staple cartridge (130) within distal jaw portion (20) of cartridge half (12). When an unspent staple cartridge (130) is seated within cartridge half (12), lockout spring (250) is deflected downwardly by a deployed swing tab (144) of staple cartridge (130) to thereby transition firing assembly (100) to a firing state. In the firing state, firing assembly (100) is freely actuatable distally, over lockout spring (250) in a deflected state, to thereby fire stapler (10). After firing is complete, firing assembly (100) is retracted proximally to its home position, thus enabling lockout spring (250) to resume its original state and bias firing assembly (100) into a lockout state until the spent staple cartridge (130) is replaced with an unspent staple cartridge (130).

When actuated distally during a firing stroke, firing assembly (100) depresses lockout spring (250) toward a floor of cartridge channel (16). In some instances, this depression can result in plastic deformation of lockout spring (250), which could undesirably inhibit the ability of lockout spring (250) to operate effectively during subsequent firings of stapler (10). Accordingly, it may be desirable to provide cartridge half (12) of stapler (10) with features that minimize the risk of such plastic deformation.

Figure 21:
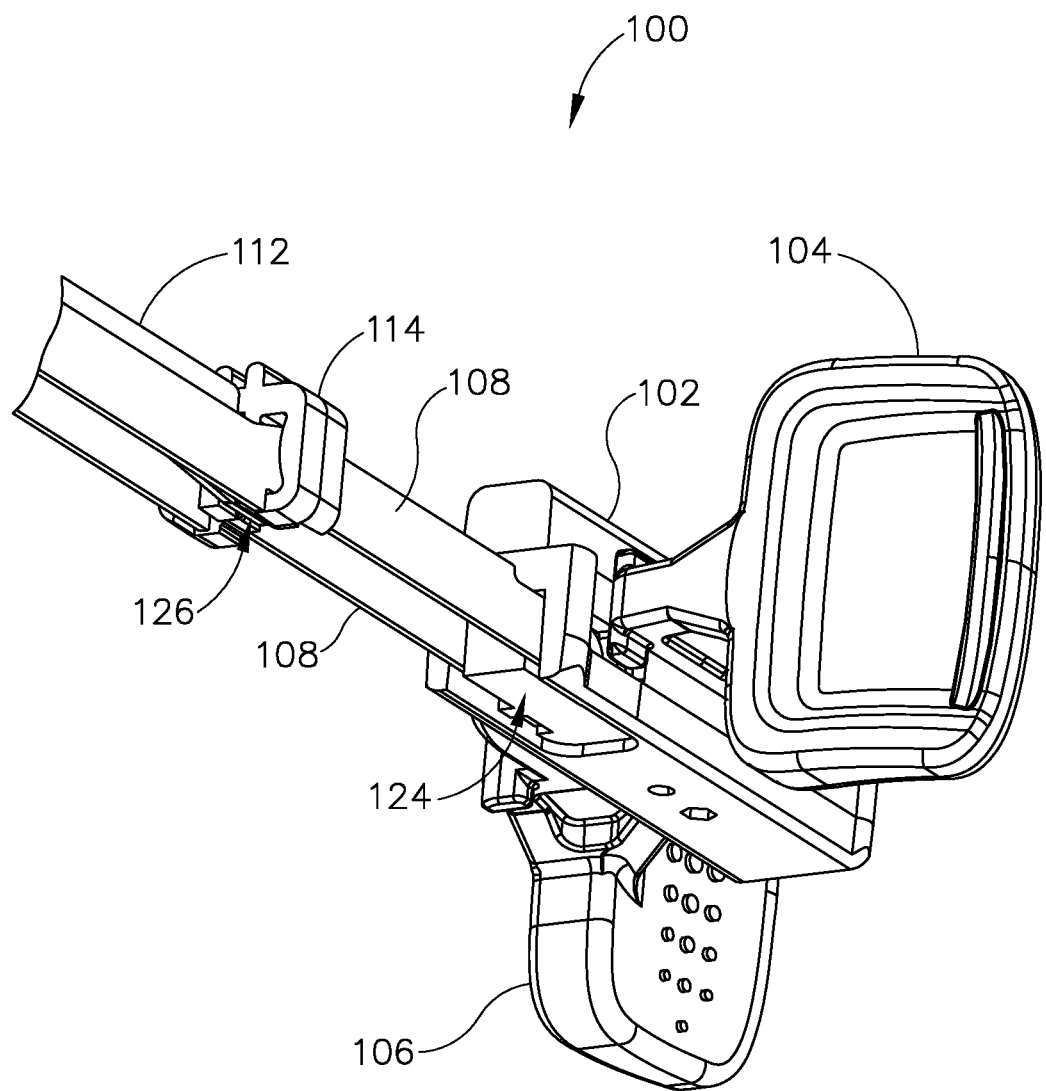
FIG. 21 depicts a perspective view of an underside of a proximal portion of the firing assembly of FIG. 4, configured for use with the linear surgical stapler of FIG. 1.

As shown in FIG. 21, an underside of slide block (102) of firing assembly (100) includes a first recess (124) that opens to a distal end of slide block (102) and extends proximally. Additionally, an underside of bridge element (114) includes a second recess (126) that extends through a full axial thickness of bridge element (114). As described below, these underside recesses (124, 126) are configured to receive a portion of lockout spring (250) when firing assembly (100) is actuated distally to a fully fired state, and thereby aid in reducing the amount by which lockout spring (250) is forced to deflect during a firing stroke.

A. Exemplary Firing Lockout System of Linear Surgical Stapler

Figure 22:
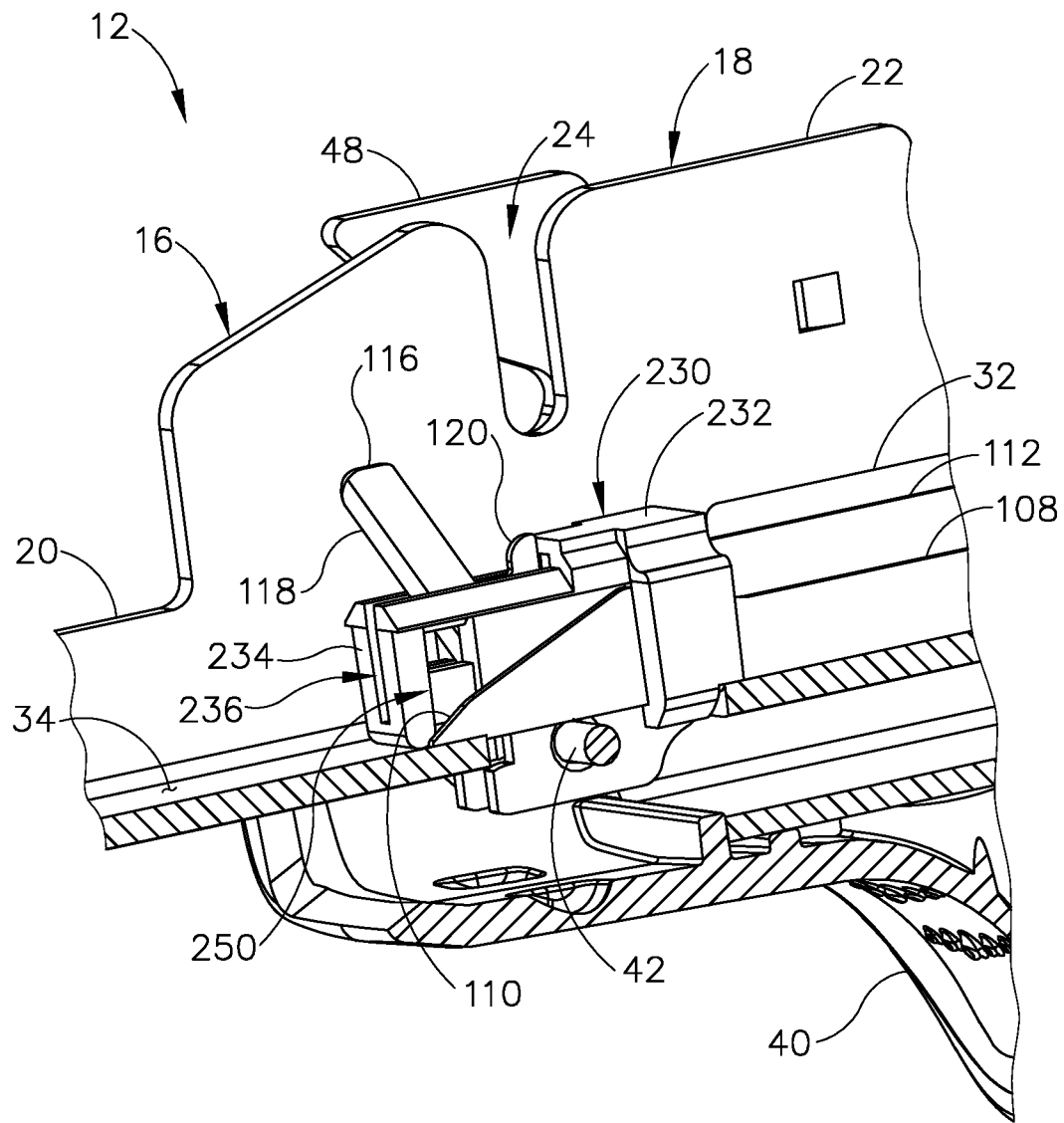
FIG. 22 depicts an enlarged cross-sectional perspective view of a portion of the cartridge half of the linear surgical stapler of FIG. 1, showing an exemplary guide block through which firing beams of the firing assembly are configured to translate.
Figure 23:
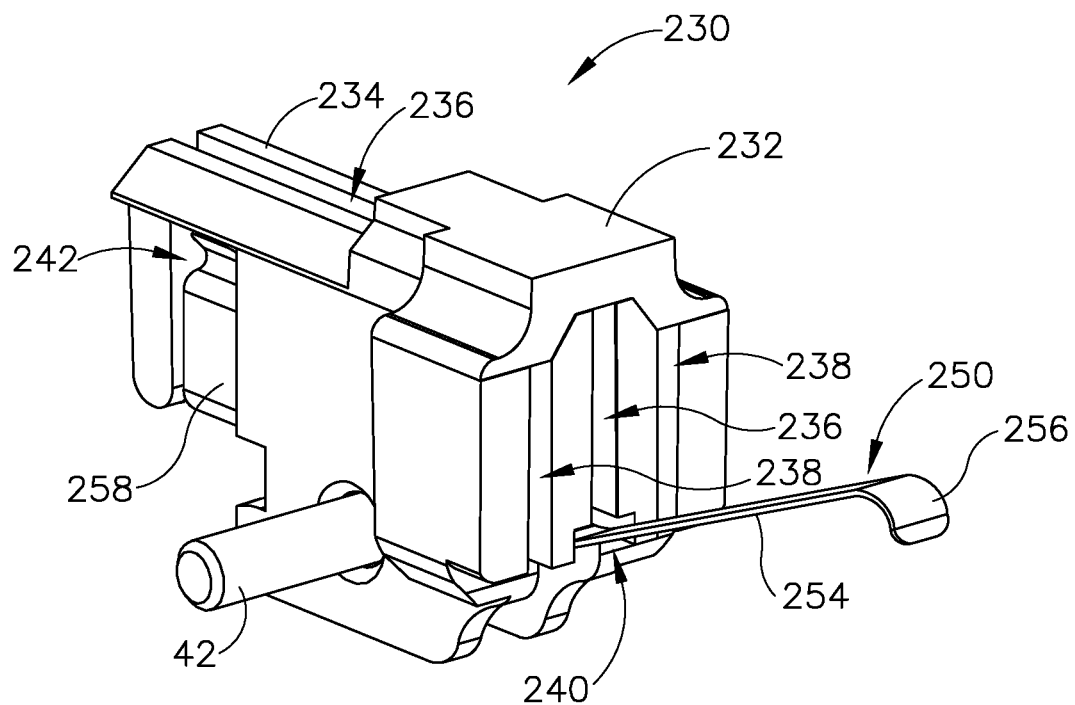
FIG. 23 depicts a perspective view of the guide block and a lockout spring of the cartridge half of FIG. 22.
Figure 24:
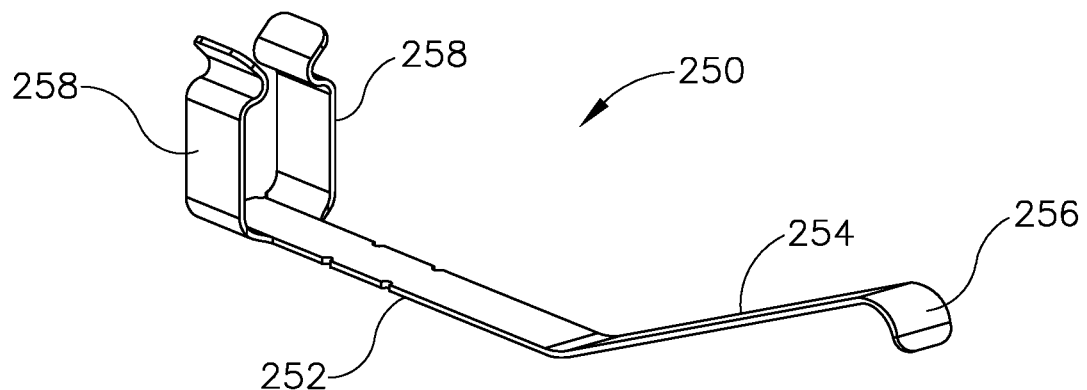
FIG. 24 depicts a perspective view of the lockout spring of FIG. 23.
Figure 25:
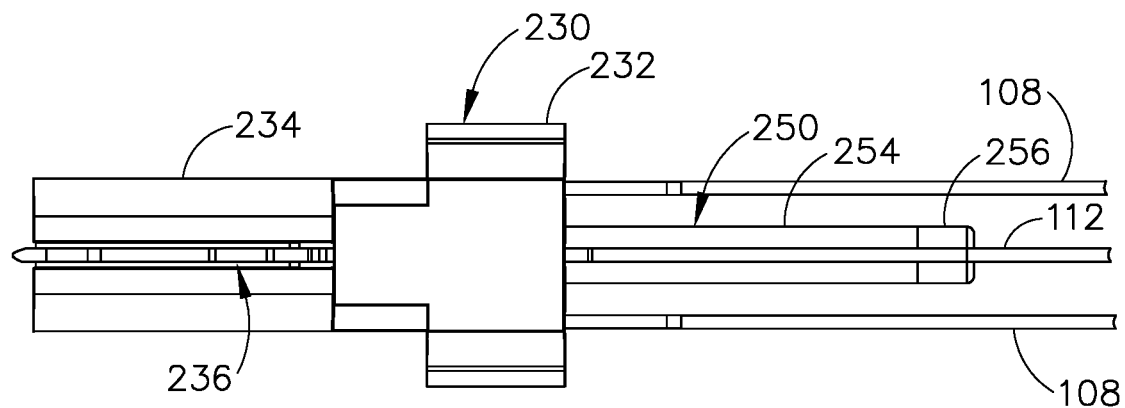
FIG. 25 depicts a top plan view of the guide block, the lockout spring, and the firing beams of the configuration of FIG. 22.

As shown in FIG. 22-24, cartridge half (12) of linear surgical stapler (10) comprises a firing lockout system that includes a guide block (230) (also referred to as a "spacer block") and lockout spring (250). Guide block (230) is secured to a floor (34) of cartridge channel (16) in approximate alignment with distal slots (24) via clamp lever pivot pin (42), which extends laterally through openings formed in guide block (230).

As shown in FIG. 23, guide block includes a proximal body portion (232) having a first lateral width, and a distal body portion (234) having a narrowed second width. A center slot (236) extends longitudinally through proximal and distal body portions (232, 234) along a centerline of guide block (230) and is configured to slidably receive center beam (112) of firing assembly (100) therethrough. A distal portion of center slot (236) opens through an upper side of distal body portion (234) and is configured to slidably receive knife member (116), as shown in FIG. 22. A pair of side slots (238) extend longitudinally through proximal body portion (232) along either side of center slot (236) and are configured to slidably receive side beams (108) of firing assembly (100) therethrough. As shown best in FIGS. 23 and 27A-27C, proximal body portion (232) further includes a lower channel (240) that extends longitudinally along a bottom end of center slot (236). As described in greater detail below, lower channel (240) is sized with a transverse dimension suitable to permit upward deflection of a base arm (252) of lockout spring (250) within lower channel (240) during firing of stapler (10). Distal body portion (234) includes a laterally opposed pair of recesses (242) configured to receive and retain a pair of distal anchor clips (258) of lockout spring (250).

As shown best in FIG. 23, lockout spring (250) is shown in the form of an elongate leaf spring having a flat base arm (252) and a spring leg (254) extending proximally from base arm (252) at an upward angle and having a downwardly curved tip (256). A pair of anchor clips (258) extend upwardly from a distal end of base arm (252). As shown in FIGS. 23 and 27A-27C, anchor clips (258) clasp against distal body portion (234) within distal recesses (242), and base arm (252) extends proximally along an underside of distal body portion (234), over clamp lever pivot pin (42), and through lower channel (240) of proximal body portion (232). Angled spring leg (254) extends proximally from lower channel (240) in longitudinal alignment with center slot (236).

Figure 26:
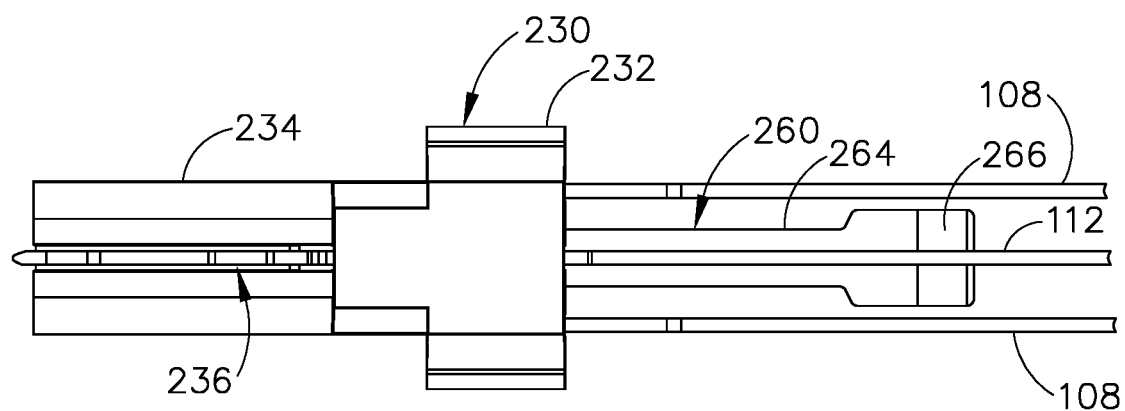
FIG. 26 depicts a top plan view of another exemplary lockout spring in combination with the guide block and the firing beams of the configuration of FIG. 22.

As shown in FIGS. 25 and 27A-27C, center beam (112) of firing assembly (100) is positioned longitudinally over spring leg (254) of lockout spring (250) such that center beam (112) is configured to translate over and in direct contact with spring leg (254). FIG. 26 shows an exemplary alternative lockout spring (260) that is similar to lockout spring (250) except that lockout spring (260) includes a downwardly curved proximal tip (266) that is wider than at least medial and distal portions of spring leg (264). Widened tip (266) is configured to maintain center beam (112) in engagement with spring leg (264) throughout longitudinal actuations of firing assembly (100).

Figure 27A:
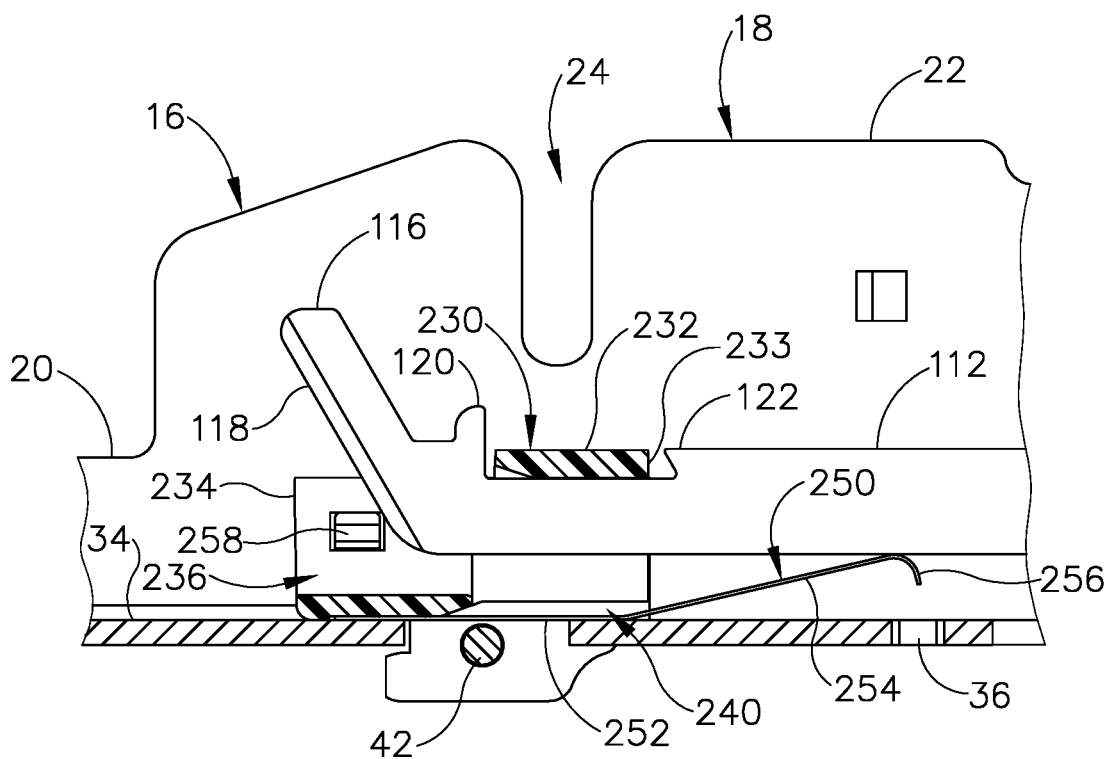
FIG. 27A depicts an enlarged side cross-sectional view of the cartridge half of the linear surgical stapler of FIG. 1, showing a knife beam of the firing assembly in a raised lockout position relative to the guide block prior to insertion of an unspent staple cartridge.
Figure 27B:
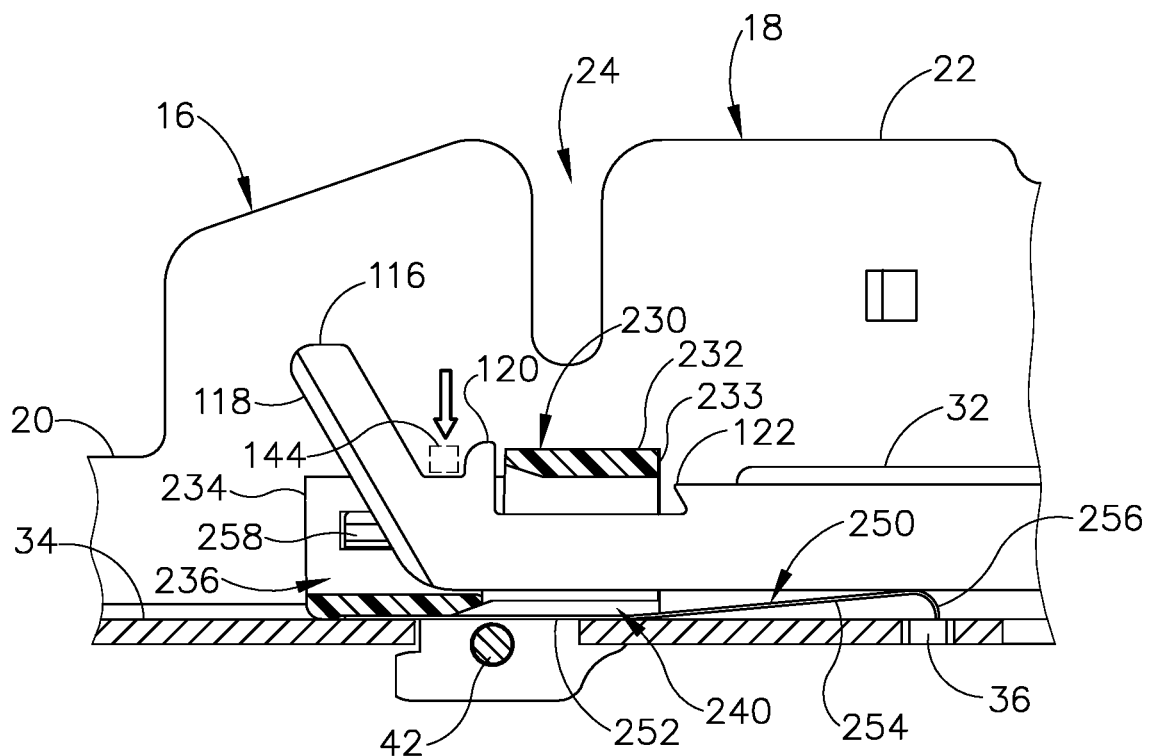
FIG. 27B depicts an enlarged side cross-sectional view of the cartridge half of the linear surgical stapler of FIG. 1, showing the knife beam in a lowered firing position relative to the guide block following insertion of an unspent staple cartridge, which is represented by schematic depiction of an extended swing tab thereof.

As shown in FIG. 27A, in the absence of an unspent staple cartridge (130) from cartridge channel (16), spring leg (254) resiliently biases center beam (112) upwardly such that lockout projection (122) of center beam (112) engages a proximal face (233) of guide block (230). This engagement locks center beam (112) longitudinally relative to guide block (230) and thus inhibits distal translation of firing assembly (100). FIG. 27B shows center beam (112) being pivoted downwardly toward cartridge channel floor (34) upon seating of an unspent staple cartridge (130) within cartridge channel (16). It will be understood that unspent staple cartridge (130) is represented in FIGS. 27B and 30B by the schematic depiction of swing tab (144) in the deployed position. As described above, swing tab (144) in the deployed position extends transversely across knife slot (142) of staple cartridge (130). Accordingly, seating of unspent staple cartridge (130) within cartridge channel (16) causes swing tab (144) to engage the upper surface of center beam (112), between knife member (116) and stop element (120), and drive center beam (112) downwardly to provide firing assembly (100) in a firing state. Seating of unspent staple cartridge (130) within cartridge channel (16) thus compresses spring leg (254) of lockout spring (250) downwardly toward cartridge floor (34).

Figure 27C:
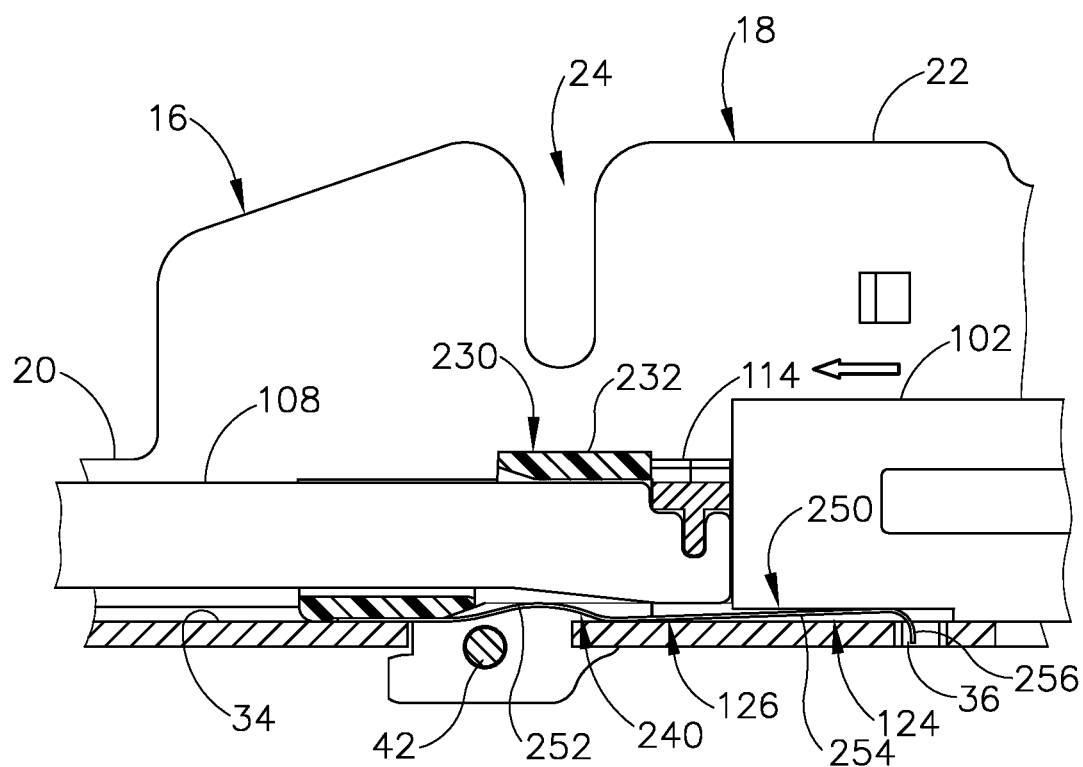
FIG. 27C depicts an enlarged side cross-sectional view of the cartridge half of the linear surgical stapler of FIG. 1, showing distal actuation of the firing assembly over the lockout spring.
Figure 28:
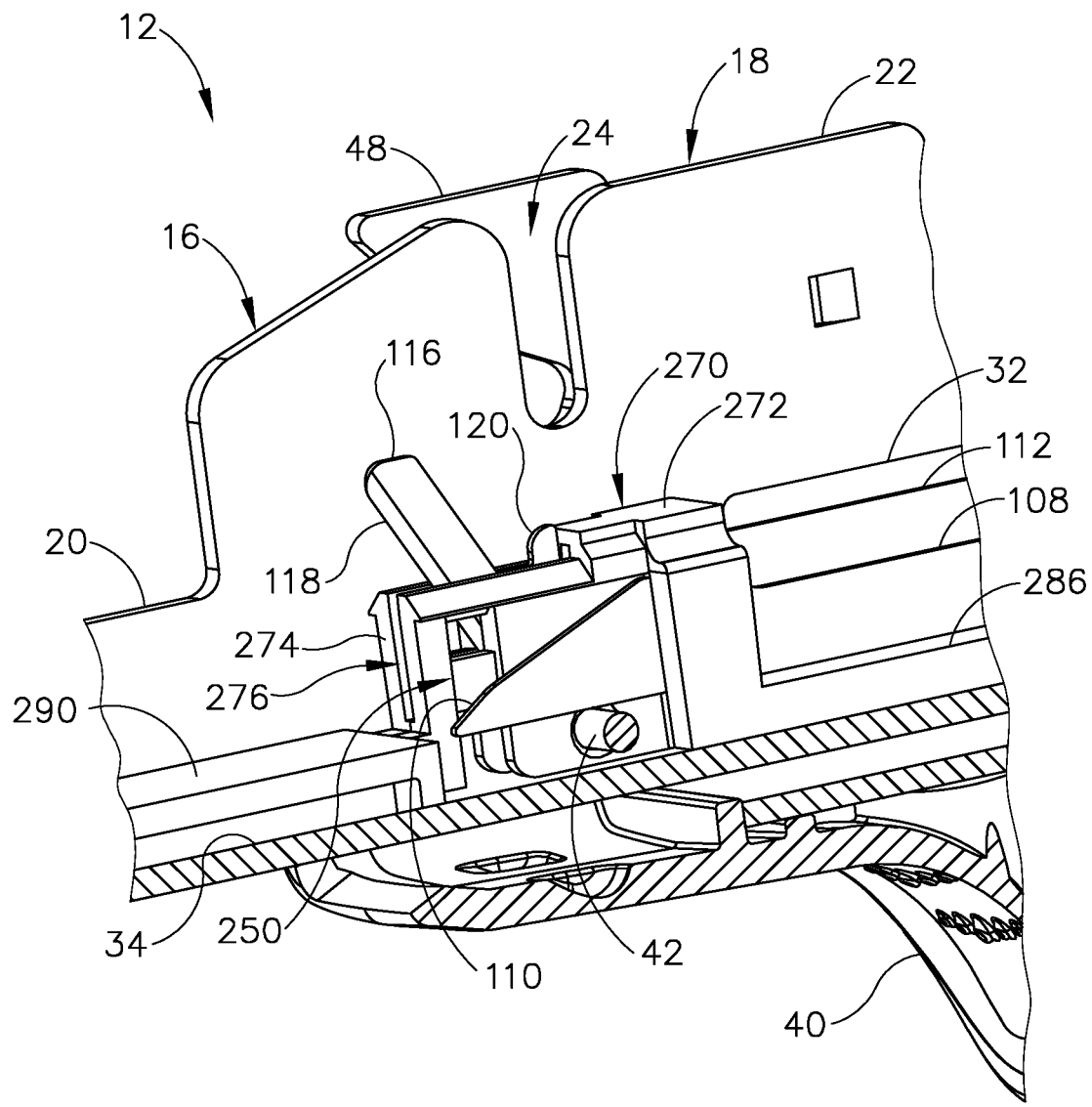
FIG. 28 depicts an enlarged cross-sectional perspective view of a portion of the cartridge half of the linear surgical stapler of FIG. 1, showing an exemplary alternative guide block through which firing beams of the firing assembly are configured to translate.
Figure 29:
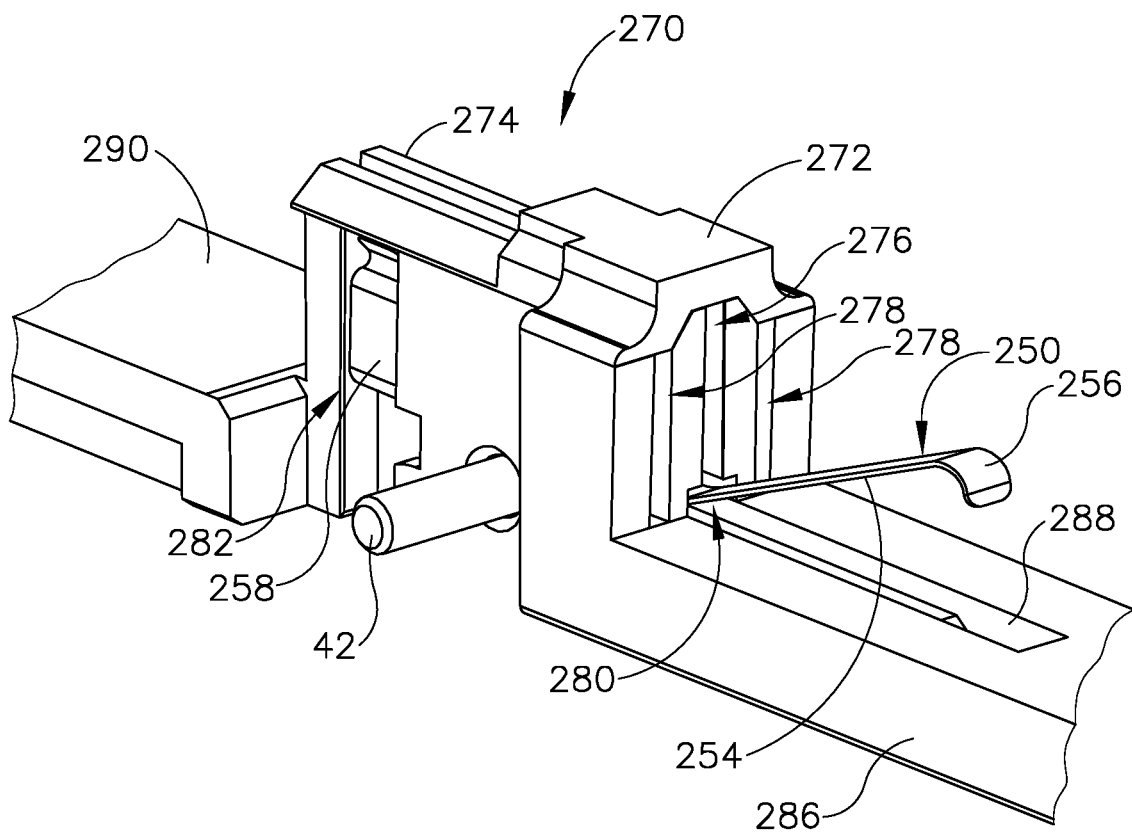
FIG. 29 depicts a perspective view of the guide block and the lockout spring of the cartridge half of FIG. 28.

As shown in FIG. 27C, firing assembly (100) in the firing state is then driven distally by an actuator (104, 106) of slide block (102) (see FIG. 4). This forces firing beams (108, 112) to translate distally through guide block (230) and into staple cartridge (130), thus actuating staple drivers (180) upwardly to drive staples (170) into tissue and simultaneously cutting the tissue with knife member (116). As firing assembly (100) advances distally toward the fully fired position shown in FIG. 27C, over spring leg (254), spring leg (254) is received through underside recess (126) of bridge element (114) and into underside recess (124) of slide block (102). Additionally, spring arm tip (256) is received into an opening (36) formed in cartridge channel floor (34). Simultaneously, base arm (252) of lockout spring (250) is permitted to resiliently deflect upwardly within lower channel (240) of guide block (230), which is also enabled by the ability of spring leg (254) to slide longitudinally as needed within underside recesses (124, 126) of firing assembly (100). In this manner, lockout spring (250) is enabled to assume a deflected state that minimizes plastic deformation thereof in the fully fired state of firing assembly (100).

B. Exemplary Alternative Firing Lockout System

In some instances, it may be desirable to alternatively configure guide block (230) described above in other manners suitable to mitigate plastic deformation of lockout spring (250) when linear surgical stapler (10) is fired. FIGS. 28-30C show cartridge half (12) fitted with an exemplary alternative guide block (270) (or "spacer block") that is similar to guide block (230) described above except as otherwise described below. In that regard, it will be understood that guide block (270) may be substituted for guide block (230) to cooperate with lockout spring (250) and other components of cartridge half (12) described above to define a firing lockout system of linear surgical stapler (10).

Guide block (270) is secured to cartridge channel floor (34) and includes a proximal body portion (272) having a first lateral width and a distal body portion (274) having a narrowed second width, a center slot (276) extending longitudinally through proximal and distal body portions (272, 274), and a pair of side slots (278) extending longitudinally through proximal body portion (272) along either side of center slot (276). Proximal body portion (272) further includes a lower channel (280) that extends longitudinally along a bottom end of center slot (276). Distal body portion (274) includes a laterally opposed pair of recesses (282) configured to receive and retain distal anchor clips (258) of lockout spring (250).

Figure 30A:
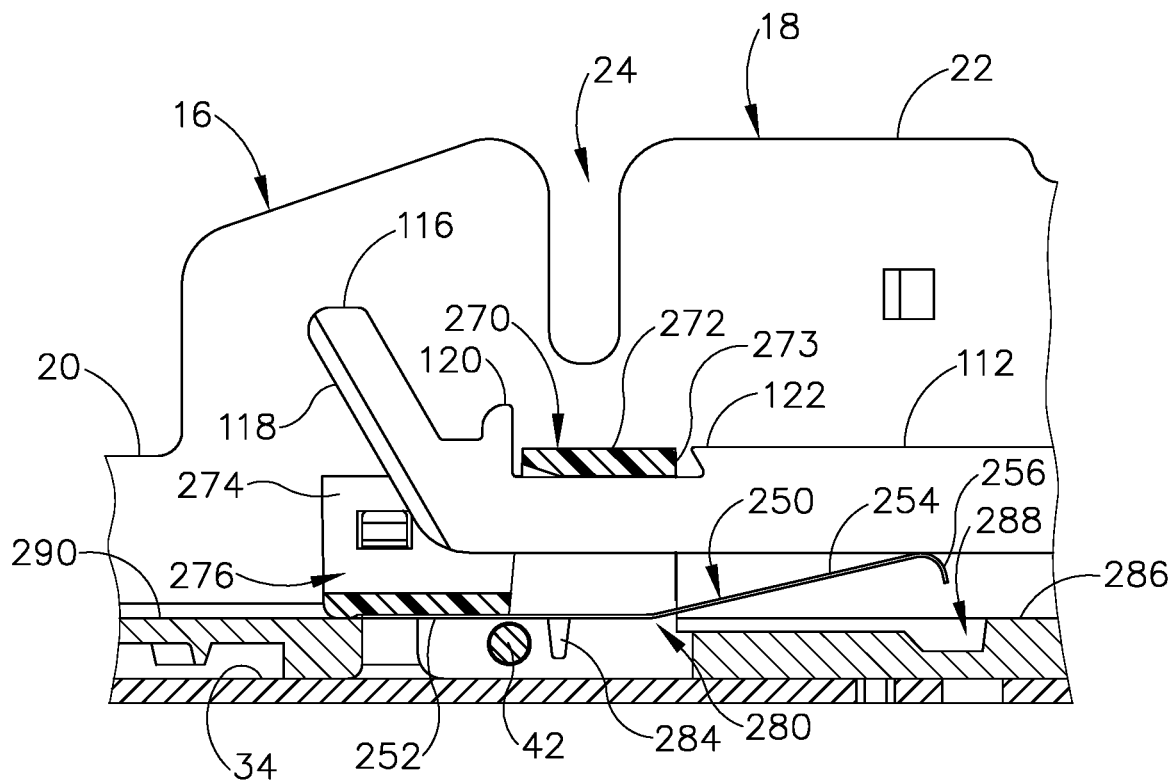
FIG. 30A depicts an enlarged side cross-sectional view of the cartridge half of FIG. 28, showing the knife beam of the firing assembly in a raised lockout position relative to the guide block prior to insertion of an unspent staple cartridge.
Figure 30B:
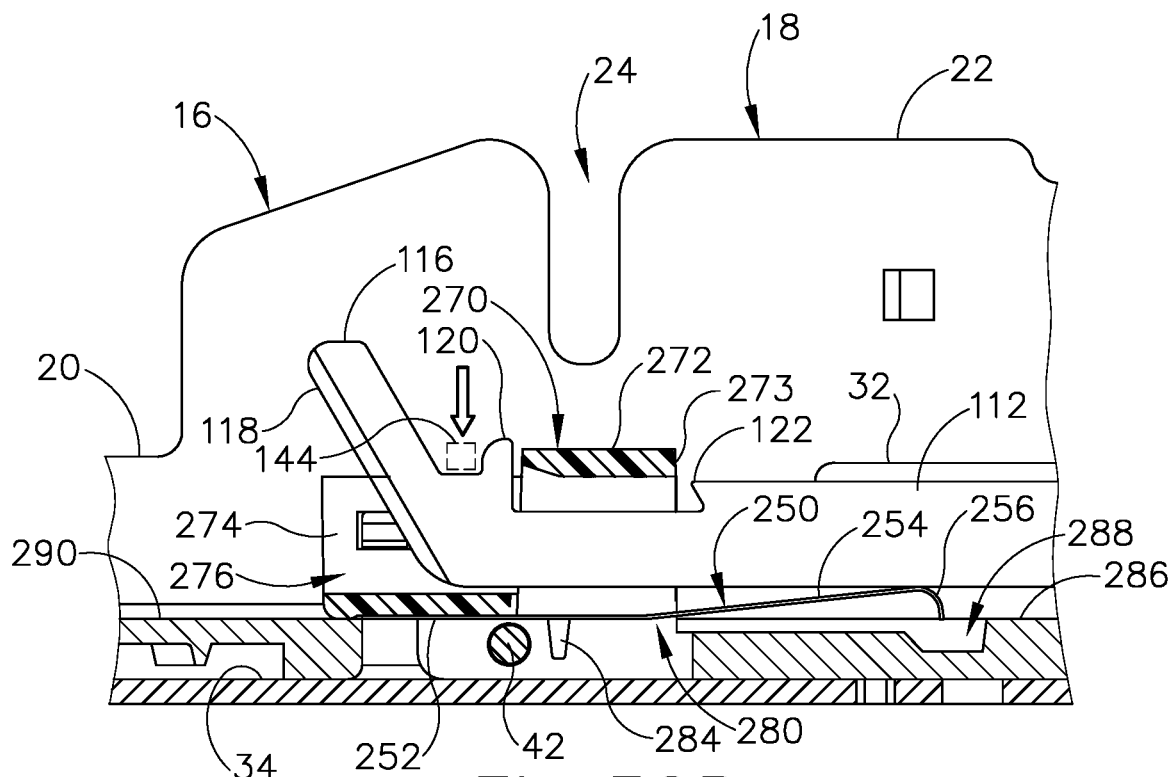
FIG. 30B depicts an enlarged side cross-sectional view of the cartridge half of FIG. 28, showing the knife beam in a lowered firing position relative to the guide block following insertion of an unspent staple cartridge, which is represented by schematic depiction of an extended swing tab thereof.

As shown in FIG. 30A, proximal body portion (272) includes a pair of spring support elements (284) projecting laterally inwardly from opposed walls of lower channel (280), proximal to clamp lever pivot pin (42). Base arm (252) of lockout spring (250) extends longitudinally through lower channel (240) such that base arm (252) is in contact with and supported vertically by clamp lever pivot pin (42) and spring support elements (284).

An elongate proximal member (286) is integrally joined with proximal body portion (272) of guide block (270) and extends proximally along cartridge channel floor (34) within proximal frame portion (18) of cartridge channel (16). An upper surface of elongate proximal member (286) includes an elongate recess (288) that communicates with lower channel (280) and is configured to receive spring leg (254) of lockout spring (250) therein when spring leg (254) is deflected downwardly during firing of stapler (10). A proximal end of elongate proximal member (286) may include a user gripping feature (not shown) that projects downwardly through an opening in cartridge channel floor (34). Such a user gripping feature may be configured to serve as a bracing point for the finger of a user so the user may use a corresponding thumb of the same hand to depress release button (90) of retaining assembly (80) distally, described above.

Figure 30C:
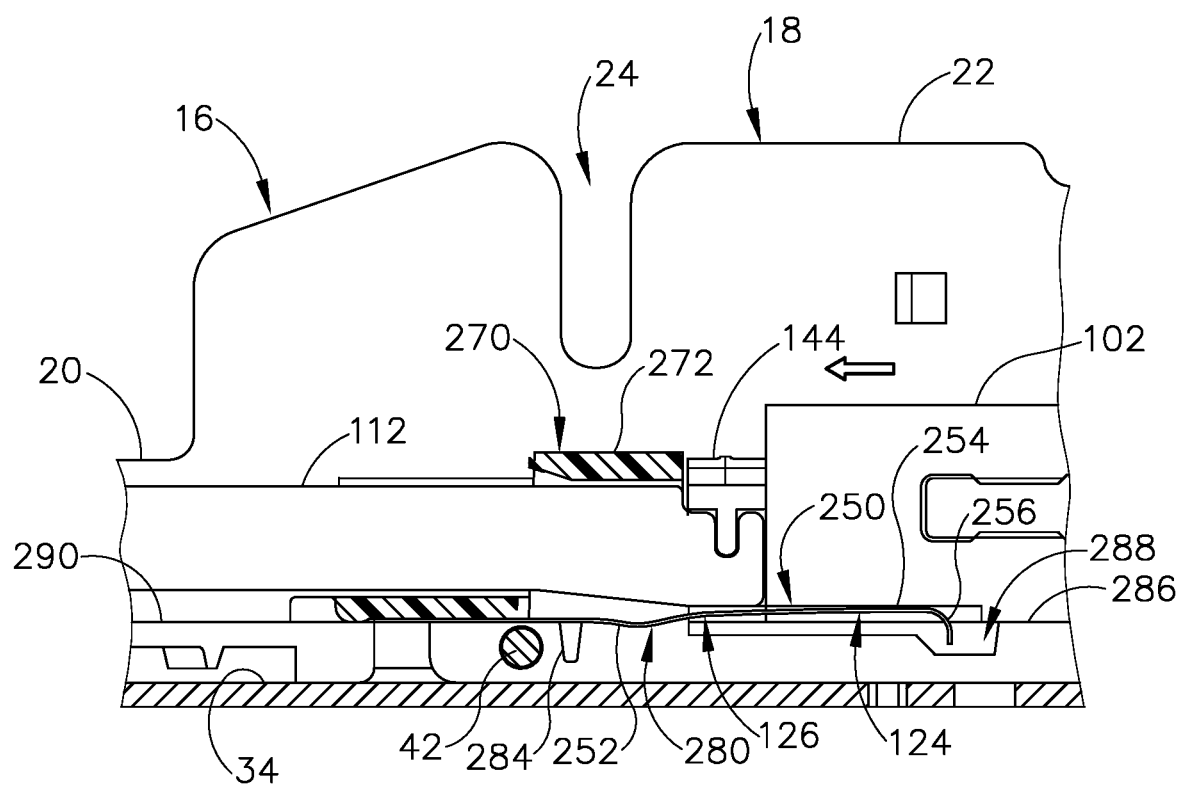
FIG. 30C depicts an enlarged side cross-sectional view of the cartridge half of FIG. 28, showing distal actuation of the firing assembly over the lockout spring.

An elongate distal member (290) is integrally joined with distal body portion (274) of guide block (270) and extends distally along cartridge channel floor (34) within distal jaw portion (20) of cartridge channel (16). A distal end of elongate distal member (290) may include a mechanical grounding feature (not shown) configured to fix elongate distal member (290) axially relative to distal jaw portion (20) of cartridge channel (16). As shown in FIGS. 30A-30C described below, firing assembly (100) is configured to translate over elongate proximal and distal members (286, 290) and through guide block (270).

As shown in FIG. 30A, in the absence of an unspent staple cartridge (130) from cartridge channel (16), spring leg (254) resiliently biases center beam (112) upwardly such that lockout projection (122) of center beam (112) engages a proximal face (273) of proximal body portion (272) of guide block (270). This engagement places firing assembly (100) in a lockout state similar to that described above in connection with FIGS. 27A-27C. FIG. 30B shows center beam (112) being pivoted downwardly toward elongate proximal member (286) by the deployed swing tab (144) of an unspent staple cartridge (130) upon seating of the unspent cartridge (130) within cartridge channel (16), thus placing firing assembly (100) in the firing state. Seating of unspent staple cartridge (130) also compresses spring leg (254) of lockout spring (250) downwardly toward elongate proximal member (286).

As shown in FIG. 30C, firing assembly (100) in the firing state is then driven distally, thus forcing firing beams (108, 112) to translate distally through guide block (270) and into staple cartridge (130), thus actuating staple drivers (180) upwardly to drive staples (170) into tissue and simultaneously cutting the tissue with knife member (116). As firing assembly (100) advances distally toward the fully fired position shown in FIG. 30C, over spring leg (254), spring leg (254) is received through underside recess (126) of bridge element (114) and into underside recess (124) of slide block (102) in a manner similar to that described above in connection with FIGS. 27A-27C. Additionally, spring leg (254) and its proximal tip (256) are received into elongate recess (288) of elongate proximal member (286). Simultaneously, as shown in FIG. 30, a medial portion of base arm (252) of lockout spring (250) is supported vertically by one or both of clamp lever pivot pin (42) and spring support elements (284), while a proximal portion of base arm (252) is permitted to resiliently deflect within lower channel (280) of guide block (270). In this manner, lockout spring (250) is enabled to assume a deflected state that minimizes plastic deformation thereof in the fully fired state of firing assembly (100).

IV. Exemplary Features to Promote Uniform Height of Formed Staples

Figure 34:
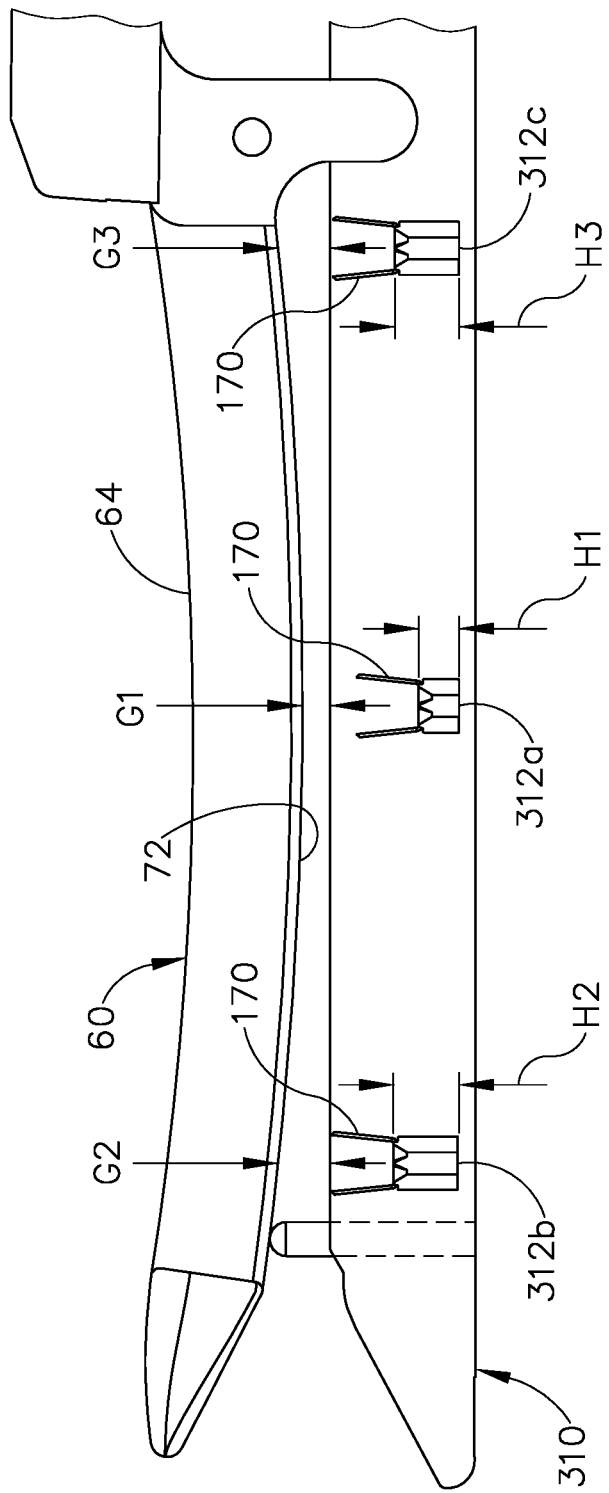
FIG. 34 depicts a schematic side elevational view of another exemplary staple cartridge and the distal portion of an anvil half of a linear surgical stapler, showing the staple cartridge having staple drivers of varying heights.

In some instances, clamping of anvil half (14) of linear surgical stapler (10) against cartridge half (12) via closure of clamp lever (40) may result in distal jaw portion (64) of anvil channel (60) deforming along its length relative to cartridge half (12). More specifically, such deformation results in anvil plate (72) and corresponding sidewall mount surfaces of distal jaw portion (64) assuming a convex curvature relative to staple cartridge deck (140) of cartridge half (12), for example as shown in FIG. 34, which depicts an exaggerated curvature of distal jaw portion (64) for illustrative purposes. As a result, the longitudinally extending tissue gap formed between staple cartridge deck (140) and anvil plate (72) may be inconsistent in size along a length of staple cartridge (130) and anvil plate (72). In particular, the tissue gap may be smaller at a medial location of staple cartridge (130) and anvil plate (72), and larger at proximal and distal end locations of staple cartridge (130) and anvil plate (72); for example as shown in FIG. 34. This inconsistency in tissue gap size can yield inconsistent heights of staples (170) formed in the clamped tissue, which is undesirable. Accordingly, it may be desirable to equip anvil half (14) and/or cartridge half (12) with features that account for such deflection of anvil channel (60) and ensure consistency in the formed height of staples (170) along a length of staple cartridge (130) and anvil plate (72).

A. Exemplary Anvil Half Having Curved Anvil Plate

Figure 31:
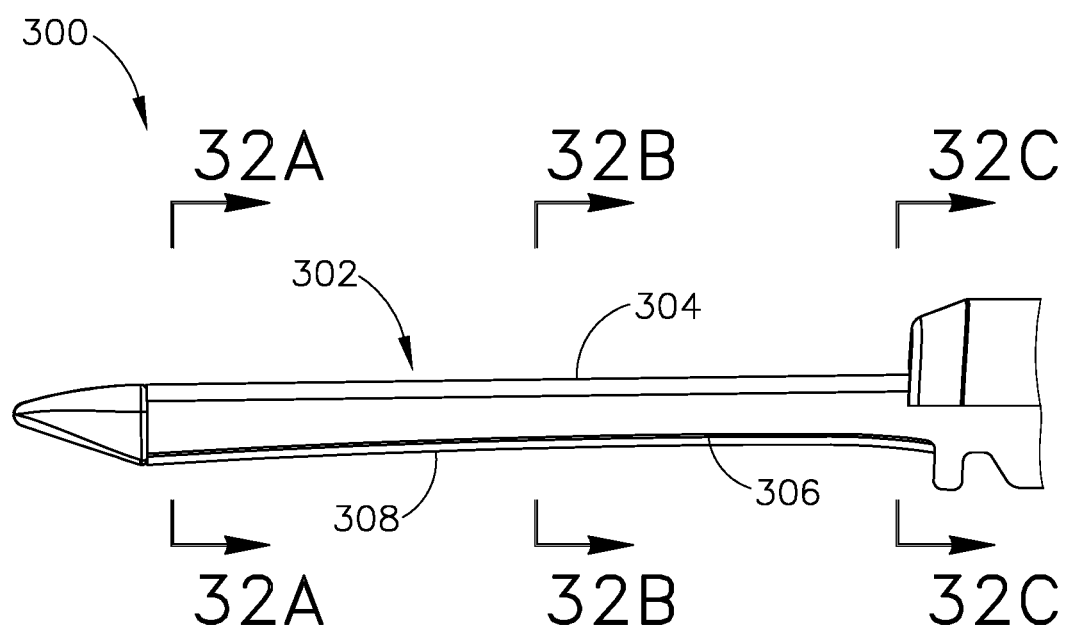
FIG. 31 depicts a side elevational view of the distal portion of another exemplary anvil half of a linear surgical stapler, showing a distal jaw portion having concavely curved mounting surfaces and an anvil plate having a similar concave curvature.

FIGS. 31-33B show an exemplary alternative anvil half (300) that is similar to anvil half (14) described above except as otherwise described below. As shown in FIG. 31, anvil half (300) includes an anvil channel (302) having a distal jaw portion (304) with a pair of sidewalls that define a pair of concavely curved mount surfaces (306) to which an anvil plate (308) is mounted. Anvil plate (308) itself conforms to the concavely curved mourn surfaces (306) of anvil channel (302), such that mount surfaces (306) and anvil plate (308) extend longitudinally along the same concavely curved path relative to a longitudinal axis of anvil half (300).

In some versions, anvil plate (308) may be initially formed with a straight, flat configuration and then deformed into a curved configuration when being compressed against and secured to curved mount surfaces (306) of anvil channel (302) (e.g., by welding) during manufacture of anvil half (302). In other versions, anvil plate (308) may be pre-formed with the same concave curvature as curved mounted surfaces (306) prior to being secured to mount surfaces (306). In either case, the concave curvature of curved mount surfaces (306), and thus of anvil plate (308), is selected as the inverse of the expected convex curvature that distal jaw portion (304) assumes relative to staple cartridge deck (140) of cartridge half (12) when stapler halves (12, 300) are fully clamped together.

As shown in FIG. 31, the concave curvature of mount surfaces (306) and anvil plate (308) in the present version is non-uniform along a length of distal jaw portion (304). Accordingly, a transverse height defined by distal jaw portion (304) in combination with anvil plate (308) varies non-uniformly along the length of distal jaw portion (304). In particular, as shown FIGS. 32A-32C, anvil half (302) exhibits a minimum transverse height (H1) at a medial location of distal jaw portion (304); a maximum transverse height (H2) at a distal end of distal jaw portion (304); and an intermediate transverse height (H3) at a proximal end of distal jaw portion (304). In some other versions, the distal and proximal transverse heights (H2, H3) may be equal.

FIG. 33A shows anvil half (302) in a partially clamped state relative to cartridge half (12) described above. In this state, the distal end of anvil plate (308) begins to clamp against tissue gap post (146) of cartridge half (12). Meanwhile, mount surfaces (306) and anvil plate (308) of anvil half (300) still exhibit a concavely curved configuration relative to deck (140) of staple cartridge (130). As shown in FIG. 33B, closing clamp lever (40) to its fully closed position forces distal jaw portion (304) of anvil channel (302) to slightly deform along its length distally of a latch pin (307). This deformation results in a flattening of mount surfaces (306) and anvil plate (308) of anvil half (302), while simultaneously producing a concave curvature in an upper surface (309) of distal jaw portion (304). Consequently, anvil plate (308) extends parallel to cartridge deck (140) and thus defines a tissue gap (G) therebetween that is uniform along the length thereof. This uniform tissue gap (G) promotes formation of staples (170) having uniform heights along the length of anvil plate (308) and cartridge deck (140).

B. Exemplary Staple Cartridge Having Staple Drivers of Varying Height

FIG. 34 schematically shows anvil channel (60) in a fully clamped state relative to an exemplary alternative staple cartridge (310). Staple cartridge (310) is similar to staple cartridge (130) described above except that staple cartridge (310) includes a plurality of staple drivers (312a, 312b, 312c) that vary in height (H1, H2, H3) along a length of staple cartridge (310). In particular, in the present version, a medial portion of staple cartridge (310) includes staple drivers (312a) of a minimum height (H1); a distal end of staple cartridge (310) includes staple drivers (312b) of a maximum height (H2); and a proximal end of staple cartridge (310) includes staple drivers (312c) of an intermediate height (H3). In some other versions, the heights (H2, H3) of distal and proximal staple drivers (312b, 312c) may be equal. Though not shown, it will be understood that the heights of staple drivers positioned between distal drivers (312b) and medial drivers (312a) may transition progressively from distal driver height (H2) to medial driver height (H1). Similarly, the heights of staple drivers positioned between medial drivers (312a) and proximal drivers (312c) may transition progressively from medial driver height (H1) to proximal driver height (H3).

As shown in FIG. 34 and as described above, distal jaw portion (64) of anvil channel (60) flexes convexly toward staple cartridge (310) when clamped against cartridge half (12). As a result, distal jaw portion (64) of anvil channel (60) assumes a curved state that yields a varying tissue gap between anvil plate (72) and staple cartridge (310) along a length thereof. In particular, a medial section of anvil plate (72) defines a minimum tissue gap (G1); a distal end of anvil plate (72) defines a maximum tissue gap (G2); and a proximal end of anvil plate (72) defines an intermediate tissue gap (G3). The provision of staple drivers (312a, 312b, 312c) of varying heights (H1, H2, H3) corrects for this variation in tissue gap (G1, G2, G3) by driving staples (170) shorter distances at the medial portion of cartridge (310) and progressively larger distances in directions advancing proximally and distally. As a result, staples (170) are formed with a uniform height along a full length of staple cartridge (310) despite the curvature of anvil channel (60) and non-uniformity in tissue gaps (G1, G2, G3).

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A staple cartridge configured for use with a surgical stapler, comprising: (a) a cartridge body; (b) a deck defined by the cartridge body, wherein the deck is configured to compress tissue against an anvil of the surgical stapler; (c) a plurality of staple openings formed in the deck; (d) a plurality of staples disposed within the staple openings, wherein each of the staples includes a pair of legs; and (e) a plurality of staple drivers disposed within the staple openings, wherein the staple drivers are actuatable to drive the staples through tissue and against the anvil to form the legs, wherein each of the staple drivers includes: (i) a driver body, (ii) a first pocket disposed on a first lateral side of the driver body, and (iii) a second pocket disposed on a second lateral side of the driver body, wherein the first and second pockets are configured to receive the legs of the respective staple when the legs are formed against the anvil.

Example 2

The staple cartridge of Example 1, wherein the first pocket and the second pocket open to an upper end of the driver body.

Example 3

The staple cartridge of any of the preceding Examples, wherein each of the staple drivers further includes a first boss disposed on the first lateral side of the driver body and a second boss disposed on the second lateral side of the driver body, wherein the first boss defines a sidewall of the first pocket, wherein the second boss defines a sidewall of the second pocket.

Example 4

The staple cartridge of any of the preceding Examples, wherein the first pocket is defined by a first chamfered surface on the first lateral side of the driver body, wherein the second pocket is defined by a second chamfered surface on the second lateral side of the body.

Example 5

The staple cartridge of Example 4, wherein upper portions of the first and second chamfered surfaces are angled toward one another.

Example 6

The staple cartridge of any of the preceding Examples, further comprising a plurality of stand-off members disposed on the deck, wherein the stand-off members project away from the deck and are configured to engage tissue.

Example 7

The staple cartridge of any of Example 6, wherein each of at least some of the stand-off members includes an end portion that wraps around a portion of an adjacent staple opening.

Example 8

The staple cartridge of Example 7, wherein the end portion includes a rounded end surface configured to confront a respective one of the staple drivers when the staple driver is actuated.

Example 9

The staple cartridge of any of Examples 6 through 8, wherein the stand-off members include a ramp feature disposed at a distal end of the deck.

Example 10

The staple cartridge of Example 9, further comprising a post disposed at a distal end of the deck, wherein the ramp feature is arranged distally of and in longitudinal alignment with the post along a longitudinal axis of the staple cartridge.

Example 11

The staple cartridge of any of the preceding Examples, further comprising: (a) an elongate slot formed in the deck, wherein the elongate slot is configured to slidably receive a cutting member therethrough, wherein the staple openings are arranged alongside the elongate slot; and (b) a pair of elongate ribs disposed on the deck, wherein the elongate ribs extend longitudinally along opposed lateral sides of the elongate slot.

Example 12

The staple cartridge of any of the preceding Examples, wherein the cartridge body extends linearly along a longitudinal axis.

Example 13

A surgical stapler comprising: (a) a first stapler half having a first distal portion that supports an anvil; (b) a second stapler half having a second distal portion; and (c) the staple cartridge of claim 1, wherein the second distal portion is configured to receive the staple cartridge, wherein the first and second stapler halves are configured to releasably couple together to clamp tissue between the anvil and the staple cartridge.

Example 14

The surgical stapler of Example 13, wherein each of the staples includes a crown from which the pair of legs extends, wherein the anvil is configured to form the legs of the staples such that leg tips of each staple are laterally offset from one another and the crown on opposed sides of the crown when the legs are formed.

Example 15

The surgical stapler of any of Examples 13 through 14, wherein the second stapler half includes: (i) a firing assembly, wherein the firing assembly is selectively actuatable distally to actuate the staple drivers to drive the staples from the staple openings, through tissue, and against the anvil, wherein an underside of the firing assembly includes a recess, and (ii) a resilient member, wherein when the staple cartridge is absent from the second distal portion, the resilient member is configured to bias the firing assembly into a lockout state and thereby inhibit distal actuation thereof, wherein when the staple cartridge is initially seated within the second elongate member, the firing assembly is configured to assume a firing state in which the firing assembly is translatable distally over the resilient member in a deflected state such that a portion of the resilient member is received within the recess of the firing assembly.

Example 16

The surgical stapler of Example 15, wherein the second stapler half further includes a guide member having a channel, wherein the resilient member extends longitudinally through the channel, wherein the resilient member is configured to resiliently deflect within the channel when the firing assembly is advanced distally.

Example 17

A staple cartridge configured for use with a surgical stapler, comprising: (a) a cartridge body; (b) a deck defined by the cartridge body, wherein the deck is configured to compress tissue against an anvil of the surgical stapler; (c) a plurality of staple openings formed in the deck; (d) a plurality of staples disposed within the staple openings, wherein each of the staples includes a first leg and a second leg; and (e) a plurality of staple drivers disposed within the staple openings, wherein the staple drivers are actuatable to drive the staples through tissue and against the anvil to form the legs, wherein each of the staple drivers includes: (i) a first lateral side having a first chamfered surface, and (ii) a second lateral side having a second chamfered surface, wherein the first chamfered surface is configured to receive the first leg of a respective staple in a confronting arrangement and the second chamfered surface is configured to receive the second leg of the respective staple in a confronting arrangement when the first and second legs are formed against the anvil.

Example 18

The staple cartridge of Example 17, wherein an upper end of each of the staple drivers is configured to support the respective staple, wherein the first and second chamfered surfaces extend to the upper end.

Example 19

A surgical stapler comprising: (a) a first elongate member having a distal portion that supports an anvil; (b) a second elongate member having a distal portion configured to receive a staple cartridge, wherein the first and second elongate members are configured to releasably couple together to clamp tissue between the anvil and the staple cartridge; (c) a guide member secured to the second elongate member; (d) a resilient member secured to the guide member; and (e) a firing assembly slidably coupled with the second elongate member, wherein an underside of the firing assembly includes a recess, wherein the guide member is configured to guide translation of a portion of the firing assembly relative to the second elongate member, wherein when a staple cartridge is absent from the second elongate member, the resilient member is configured to bias the firing assembly into a lockout state and thereby inhibit distal actuation thereof, wherein when an unspent staple cartridge is seated within the second elongate member, the firing assembly is configured to assume a firing state in which the firing assembly is translatable distally over the resilient member in a deflected state such that a proximal end of the resilient member is received within the recess of the firing assembly.

Example 20

The surgical stapler of Example 19, wherein the resilient member extends longitudinally through the guide member, wherein the resilient member is configured to resiliently deflect within the guide member when the firing assembly is advanced distally.

VI. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. application Ser. No. 15/889,363, entitled "Release Mechanism for Linear Surgical Stapler," filed on Feb. 6, 2018, issued as U.S. Pat. No. 10,631,866 on Apr. 28, 2020; U.S. application Ser. No. 15/889,370, entitled "Lockout Assembly for Linear Surgical Stapler," filed on Feb. 6, 2018, issued as U.S. Pat. No. 10,667,818 on Jun. 2, 2020; U.S. application Ser. No. 15/889,374, entitled "Features to Align and Close Linear Surgical Stapler"," filed on Feb. 6, 2018, issued as U.S. Pat. No. 10,932,781 on Mar. 2, 2021; U.S. application Ser. No. 15/889,376, entitled "Releasable Coupling Features for Proximal Portions of Linear Surgical Stapler," filed on Feb. 6, 2018, issued as U.S. Pat. No. 10,898,197 on Jan. 26, 2021; U.S. application Ser. No. 15/889,388, entitled "Firing Lever Assembly for Linear Surgical Stapler," filed on Feb. 6, 2018, issued as U.S. Pat. No. 10,874,398 on Dec. 29, 2020; U.S. application Ser. No. 15/889,390, entitled "Clamping Mechanism for Linear Surgical Stapler," filed on Feb. 6, 2018, issued as U.S. Pat. No. 10,687,819 on Jun. 23, 2020; U.S. patent application Ser. No. 16/102,164, entitled "Firing System for Linear Surgical Stapler," filed on Aug. 13, 2018, issued as 10,898,187 on Jan. 26, 2021; U.S. patent application Ser. No. 16/102,170, entitled "Clamping Assembly for Linear Surgical Stapler," filed on Aug. 13, 2018, published as U.S. Pub. No. 2020/0046353 on Feb. 13, 2020; U.S. application Ser. No. 16/157,599, entitled "Anvil Assembly for Linear Surgical Stapler," filed on Oct. 11, 2018, issued as U.S. Pat. No. 11,045,193 on Jun. 29, 2021; U.S. application Ser. No. 16/157,605, entitled "Closure Assembly for Linear Surgical Stapler," filed on Oct. 11, 2018, issued as U.S. Pat. No. 10,905,419 on Feb. 2, 2021; and/or U.S. patent application Ser. No. 16/165,587, entitled "Decoupling Mechanism for Linear Surgical Stapler," filed on Oct. 19, 2018, issued as U.S. Pat. No. 11,033,266 on Jun. 15, 2021. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A staple cartridge configured for use with a surgical stapler, comprising:
   (a) a cartridge body;
   (b) a deck defined by the cartridge body, wherein the deck is configured to compress tissue against an anvil of the surgical stapler;
   (c) a plurality of staple openings formed in the deck;
   (d) a plurality of staples disposed within the staple openings, wherein each of the staples includes a crown and a pair of legs extending from the crown; and
   (e) a plurality of staple drivers disposed within the staple openings beneath the crowns of the staples, wherein the staple drivers are actuatable to drive the staples through tissue and against the anvil to form the legs, wherein each of the staple drivers includes:
      (i) a driver body having an upper end that supports the crown of a respective staple,
      (ii) a first pocket disposed on a first exterior lateral side of the driver body and opening to the upper end, and
      (iii) a second pocket disposed on a second exterior lateral side of the driver body and opening to the upper end,
   wherein the first and second pockets are configured to receive the legs of the respective staple when the legs are formed against the anvil such that the formed legs do not contact the driver body.

2. The staple cartridge of claim 1, wherein each of the staple drivers further includes a first boss disposed on the first exterior lateral side of the driver body and a second boss disposed on the second exterior lateral side of the driver body, wherein the first boss defines a sidewall of the first pocket, wherein the second boss defines a sidewall of the second pocket.

3. The staple cartridge of claim 1, wherein the first pocket is defined by a first chamfered surface on the first exterior lateral side of the driver body, wherein the second pocket is defined by a second chamfered surface on the second exterior lateral side of the body.

4. The staple cartridge of claim 3, wherein upper portions of the first and second chamfered surfaces are angled toward one another.

5. The staple cartridge of claim 1, further comprising a plurality of stand-off members disposed on the deck, wherein the stand-off members project away from the deck and are configured to engage tissue.

6. The staple cartridge of claim 5, wherein each of at least some of the stand-off members includes an end portion that wraps around a portion of an adjacent staple opening.

7. The staple cartridge of claim 6, wherein the end portion includes a rounded end surface configured to confront a respective one of the staple drivers when the staple driver is actuated.

8. The staple cartridge of claim 5, wherein the stand-off members include a ramp feature disposed at a distal end of the deck.

9. The staple cartridge of claim 8, further comprising a post disposed at a distal end of the deck, wherein the ramp feature is arranged distally of and in longitudinal alignment with the post along a longitudinal axis of the staple cartridge.

10. The staple cartridge of claim 1, further comprising:
    (a) an elongate slot formed in the deck, wherein the elongate slot is configured to slidably receive a cutting member therethrough, wherein the staple openings are arranged alongside the elongate slot; and
    (b) a pair of elongate ribs disposed on the deck, wherein the elongate ribs extend longitudinally along opposed lateral sides of the elongate slot.

11. A surgical stapler comprising:
    (a) a first stapler half having a first distal portion that supports an anvil;
    (b) a second stapler half having a second distal portion; and
    (c) the staple cartridge of claim 1, wherein the second distal portion is configured to receive the staple cartridge,
    wherein the first and second stapler halves are configured to releasably couple together to clamp tissue between the anvil and the staple cartridge.

12. The surgical stapler of claim 11, wherein the anvil is configured to form the legs of the staples such that leg tips of each staple are laterally offset from one another and the crown on opposed sides of the crown when the legs are formed.

13. The surgical stapler of claim 11, wherein the second stapler half includes:
    (i) a firing assembly, wherein the firing assembly is selectively actuatable distally to actuate the staple drivers to drive the staples from the staple openings, through tissue, and against the anvil, wherein an underside of the firing assembly includes a recess, and
    (ii) a resilient member, wherein when the staple cartridge is absent from the second distal portion, the resilient member is configured to bias the firing assembly into a lockout state and thereby inhibit distal actuation thereof, wherein when the staple cartridge is initially seated within the second elongate member, the firing assembly is configured to assume a firing state in which the firing assembly is translatable distally over the resilient member in a deflected state such that a portion of the resilient member is received within the recess of the firing assembly.

14. The surgical stapler of claim 13, wherein the second stapler half further includes a guide member having a channel, wherein the resilient member extends longitudinally through the channel, wherein the resilient member is configured to resiliently deflect within the channel when the firing assembly is advanced distally.

15. The staple cartridge of claim 1, wherein each of the staple drivers is interconnected with an adjacent staple driver.

16. The surgical stapler of claim 11, wherein the anvil of the first stapler half is configured to extend longitudinally along a path that is concavely curved relative to a longitudinal axis of the first stapler half.

17. The surgical stapler of claim 16, wherein the first distal portion of the first stapler half has a proximal end portion that defines a first transverse height and a distal end portion that defines a second transverse height different than the first transverse height.

18. A staple cartridge configured for use with a surgical stapler, comprising:
 (a) a cartridge body;
 (b) a deck defined by the cartridge body, wherein the deck is configured to compress tissue against an anvil of the surgical stapler;
 (c) a plurality of staple openings formed in the deck;
 (d) a plurality of staples disposed within the staple openings, wherein each of the staples includes a crown and a first leg and a second leg extending from the crown; and
 (e) a plurality of staple drivers disposed within the staple openings beneath the crowns of the staples, wherein the staple drivers are actuatable to drive the staples through tissue and against the anvil to form the legs, wherein each of the staple drivers includes:
  (i) a driver body having an upper end that supports the crown of a respective staple,
  (ii) a first chamfered surface disposed on a first exterior lateral side of the driver body and extending to the upper end, and
  (iii) a second chamfered surface disposed on a second exterior lateral side of the driver body and extending to the upper end,
 wherein the first chamfered surface is configured to receive the first leg of a respective staple in a confronting and non-contacting arrangement and the second chamfered surface is configured to receive the second leg of the respective staple in a confronting and non-contacting arrangement when the first and second legs are formed against the anvil.

19. The staple cartridge of claim 18, wherein upper portions of the first chamfered surface and the second chamfered surface are angled toward one another.

20. A staple cartridge configured for use with a surgical stapler, comprising:
 (a) a cartridge body;
 (b) a deck defined by the cartridge body, wherein the deck is configured to compress tissue against an anvil of the surgical stapler;
 (c) a plurality of staple openings formed in the deck;
 (d) a plurality of staples disposed within the staple openings, wherein each of the staples includes a crown and a pair of legs extending from the crown; and
 (e) a plurality of staple driver units disposed within the cartridge body beneath the crowns of the staples, wherein the staple driver units are actuatable to drive the staples through tissue and against the anvil to form the legs, wherein each staple driver unit includes an interconnected pair of staple drivers that align with respective staple openings, wherein each of the staple drivers includes:
  (i) a driver body having an upper end that supports the crown of a respective staple,
  (ii) a first staple leg receiving feature disposed on a first exterior lateral side of the driver body, and
  (iii) a second staple leg receiving feature disposed on a second exterior lateral side of the driver body,
 wherein the first and second staple leg receiving features are configured to receive the legs of the respective staple when the legs are formed against the anvil such that the formed legs confront but do not contact the driver body.

* * * * *